United States Patent
Montangnier et al.

(10) Patent No.: US 6,440,657 B1
(45) Date of Patent: *Aug. 27, 2002

(54) NUCLEIC ACIDS AND PEPTIDES OF HUMAN IMMUNODEFICIENCY VIRUS TYPE (HIV-1)

(75) Inventors: Luc Montangnier, Le Plessis Robinson; Bernard Krust, Paris; Solange Chamaret, Paris; François Clavel, Paris; Jean-Claude Chermann, Elancourt; Françoise Barre-Sinoussi, Issy les Moulineaux; Marc Alizon; Pierre Sonigo, both of Paris; Stewart Cole, Chatillon; Olivier Danos, Paris; Simon Wain-Hobson, Montigny les Bretonneux, all of (FR)

(73) Assignees: Institut Pasteur; Centre National de la Recherche Scientifique, both of Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/478,492

(22) Filed: Jan. 6, 2000

Related U.S. Application Data

(63) Continuation of application No. 08/466,920, filed on Jun. 6, 1995, now abandoned, which is a continuation of application No. 08/130,565, filed on Oct. 1, 1993, now abandoned, which is a division of application No. 07/970,954, filed on Nov. 3, 1992, now abandoned, which is a continuation of application No. 07/747,506, filed on Aug. 20, 1991, now abandoned, which is a continuation of application No. 07/622,278, filed on Dec. 6, 1990, now abandoned, which is a continuation of application No. 07/390,499, filed on Aug. 1, 1989, now abandoned, which is a continuation of application No. 06/920,119, filed on Oct. 17, 1986, now abandoned, which is a continuation-in-part of application No. 06/771,248, filed on Aug. 30, 1985, now abandoned, which is a continuation-in-part of application No. 06/771,247, filed on Aug. 30, 1985, now abandoned, which is a continuation-in-part of application No. 06/771,230, filed on Aug. 30, 1985, now abandoned, which is a continuation-in-part of application No. 06/706,562, filed on Feb. 28, 1985, now abandoned, which is a continuation-in-part of application No. 06/558,109, filed on Dec. 5, 1983, now abandoned.

(30) Foreign Application Priority Data

Nov. 16, 1984 (GB) ............................................. 8429099
Oct. 18, 1985 (CA) ............................................. 493377

(51) Int. Cl.$^7$ ............................................. C12Q 1/70
(52) U.S. Cl. .................... 435/5; 435/7.1; 424/188.1; 424/208.1
(58) Field of Search .................. 435/5, 7.1; 530/300, 530/324–328; 424/188.1, 208.1

(56) References Cited

U.S. PATENT DOCUMENTS 4,725,669 A 2/1988 Essex et al.
4,843,011 A 6/1989 Sarngadharan
4,956,273 A 9/1990 Kennedy
5,165,949 A 11/1992 Luciw et al.
5,980,900 A * 11/1999 Alizon et al. ............. 424/188.1

FOREIGN PATENT DOCUMENTS

EP 0 138 667 4/1985

OTHER PUBLICATIONS

Montagnier, et al., "Identification and Antigenicity of the Major Envelope Glycoprotein of Lymphadenopathy–Associated Virus," Virology 144, 283–289 (1985).

Barin et al., "Virus Envelope Protein of HTLV–III Represents Major Target Antigen for Antibodies in Aids Patients," Science, 228, 1094–1096 (1985).

Allan et al., "Major Glycoprotein Antigens That Incduce Antibodies in AIDS Patients Are Encoded by HTLV–III," Science, 228, 1091–1094 (1985).

Pauletti et al., "Application of a Modified Computer Algorithm in Determining Potential Antigenic Determinants Associated with the Aids Virus Glycoprotein," Analytical Biochemistry, 151, 540–546 (1985).

Sarngadharan et al., "Immunological Properties of HTLV–III Antigens Recognized by Sera of Patients with AIDS and AIDS–Related Complex and Asymptomatic Carriers of HTLV–III Infection," Cancer Research, 45, 4574s–4577s (1985).

Robey et al., "Characterization of Envelope and Core Structural Gene Products of HTLV–III with Sera from AIDS Patients," Science, 228, 593–595 (1985).

Wain–Hobson et al., "Nucleotide Sequence of the AIDS Virus, LAV," Cell, 40, 9–17 (1985).

(List continued on next page.)

*Primary Examiner*—Laurie Scheiner
*Assistant Examiner*—Jeffrey S. Parkin
(74) *Attorney, Agent, or Firm*—Finnegan, Henderson, Farabow, Garrett & Dunner, L.L.P.

(57) ABSTRACT

The molecular cloning and characterization of a novel human retrovirus, designated lymphadenopathy-associated virus, or LAV, is disclosed. LAV was originally isolated from a patient with acquired immune deficiency syndrome (AIDS). A cloned LAV complementary DNA (cDNA) was used to screen a library of recombinant phages constructed from the genomic DNA of LAV-infected T lymphocytes. The nucleotide sequence of an insert obtained from the recombinant phage clone λJ19 was ascertained through M13 shotgun cloning and the dideoxy chain termination sequencing method. The env coding region was identified and various hydrophilic peptides obtained therefrom. These peptides correspond to amino acids 551–577, 594–603, 621–630, 657–679, and 719–758 of the LAV envelope glycoprotein. These peptides should provide suitable diagnostic reagents for the detection LAV-specific antibodies and for the generation of LAV-specific immunological reagents.

6 Claims, 15 Drawing Sheets

OTHER PUBLICATIONS

Muesing et al., "Nucleic Acid Structure and Expression of the Human AIDS/Lymphadenopathy Retrovirus," Nature, 313, 450–458 (1985).

Sanchez–Pescador at al., "Nucleotide Sequence and Expression of an AIDS–Associated Retrovirus (ARV–2)," Science, 227, 484–492 (1985).

Ratner et al., "Complete Nucleotide Sequence of the AIDS Virus, HTLV–III," Nature, 313, 277–284 (1985).

Chang et al., "An HTLV–III Peptide Produced By Recombinant DNA is Immunoreactive with Sera from Patients with AIDS," Nature, 315, 151–154 (1985).

Dowbenko et al., "Bacterial Expression of the Acquired Immunodeficiency Syndrome Retrovirus p24 gag Protein and its use as a Diagnostic Reagent," Proc. Natl. Acad. Sci. USA, 82, 7748–7752 (1985).

Chang et al., "Detection of Antibodies to Human T–Cell Lymphotropic Virus–III (HTLV–III) with an Immunoassay Employing a Recombinant *Escherichia coli*–Derived Viral Antigenic Peptide," Bio/Technology, 3 905–909 (1985).

Chang et al., "Expression in *Escherichia coli* of Open Reading Frame Gene Segments of HTLV–III," Science, 228, 93–96 (1985).

Schneider et al., "A Glycopolypeptide (gp 100) is the Main Antigen Detected By HTLV–III Antisera," Med. Microbiol. Immunol., 174, 35–42 (1985).

Casey et al., Virology, 55 (2), 417–423 (1985).

* cited by examiner

```
CysLysThrIleLeuLysAlaLeuGlyProAlaAlaThrLeuGluGluMetMetThrAlaCysGlnGlyValGlyGlyProGlyHisLysAlaArgValLeuAlaGluAlaMetSerGln
ATTGTAAGACTATTTTAAAGACATTGGGACCAGCAGCTACACTGGAAGAAATGATGACAGCATGTCAGGGAGTGGGAGGACCCGGCCATAAGGCCAGAGAGTTTTGGCTGAAGCAATGAGCC
                                                         1400
ValThrAsnSerAlaThrIleMetMetGlnArgGlyAsnPheArgAsnGlnArgLysIleValLysCysPheAsnCysGlyLysGluGlyHisIleAlaArgAsnCysArgAlaProArg
AAGTAACAAATTCAGCTACCATAATGATGCAAAGAGGCAATTTAGGAACCAAAGAAAGATTGTTAAGTGTTTCAATTGTGGCAAAGAAGGGCACATAGCCAGAAATTGCAGGGCCCCTA
                                            1500                          POL → PhePheArgGluAspLeuAlaPheLeuGlnGlyLysAlaArgGluPheSer
LysLysGlyCysTrpLysCysGlyLysGluGlyHisGlnMetLysAspCysThrGluArgGlnAlaAsnPheLeuGlyLysIleTrpProSerTyrLysGlyArgProGlyAsnPheLeu
GGAAAAAGGGCTGTTGGAAATGTGGAAAGGAAGGACACCAAATGAAAGATTGTACTGAGAGACAGGCTAATTTTTAGGAAGATCTGGCCTTCTACAGGGAAGGCCAGGGAATTTC
                            1600
SerGlnThrArgAlaAsnSerProThrArgArgGluLeuGlnValTrpGlyArgAspAsnAsnSerLeuSerGluAlaGlyAlaAspArgGlnGlyThrValSer-PheAsnPhePro
GlnSerArgProGlnThrAlaProProGluProThrAlaProProGluSerPheArgSerGlyValGluThrThrProSerGlnLysGlnGluProIleAspLysGluLeuTyrProLeuThrSerLeu
TTCAGAGACCAGACCAGAGCCAACAGCCCCAGCCACCAGAGCCAACAGCCCCTCAGAACCCCTCCAGAAGCCCATAGACACAAGGACCGATAGACCAGGAGACCAGGAGAACTGTATCCCTTTAACTTCCC
       1700                                                                                   1800
GlnIleThrLeuTrpGlnArgProLeuValThrIleLysIleGlyGlyGlnLeuLysGluAlaLeuLeuAspThrGlyAlaAspAspThrValLeuGluMetSerLeuProGlyArg
TCAGATCACTCTTTGGCAACGACCCCTCGTCACAATAAAGATAGGGGGGCAACTAAAGGAAGCTCTATTAGATACAGGAGCAGATGATACAGTATTAGAAGAAATGAGTTTGCCAGGAAG
ArgSerLeuPheGlyAsnAspProSerSerGln *
                                            1900
```

NUCLEIC ACIDS AND PEPTIDES OF HUMAN IMMUNODEFICIENCY VIRUS TYPE (HIV-1)

CROSS-REFERENCE TO RELATED APPLICATIONS

This is a continuation of application Ser. No.08/466,920, filed Jun. 6, 1995 (now abandoned), which is a continuation of application Ser. No. 08/130,565 , filed Oct. 1, 1993, (now abandoned) which is a division of application Ser. No. 07/970,954, filed Nov. 3, 1992, (now-abandoned), which is a continuation of application Ser. No. 07/747,506 filed Aug. 20, 1991 (now abandoned), which is a continuation of application Ser. No. 07/622,278, filed Dec. 6, 1990 (now abandoned), which is a continuation of application Ser. No. 07/390,499, filed Aug. 1, 1989 (now abandoned), which is a continuation of application Ser. No. 06/920,119, filed Oct. 17, 1986 (now abandoned), which is a continuation-in-part of application Ser. No. 06/771,248, filed Aug. 30, 1985 (now abandoned), which is a continuation-in-part of application Ser. No. 06/771,247, filed Aug. 30, 1985 (now abandoned), which is a continuation-in-part of application Ser. No. 06/771,230, filed Aug. 30, 1985 (now abandoned), which is a continuation-in-part of application Ser. No. 06/706,562, filed Feb. 28, 1985 (now abandoned), which is a continuation-in-part of application Ser. No. 06/558,109, filed Dec. 5, 1983 (now abandoned), all of which are incorporated herein by reference.

FIELD OF THE INVENTION

The present invention relates to antigens, particularly in a purified form, of the virus of lymphadenopathies (denoted below by the abbreviation LAS) and of the acquired immuno-depressive syndrome (denoted below by the abbreviation AIDS), to a process for producing these antigens, particularly antigens of the envelopes of these viruses. The invention also relates to polypeptides, whether glycosylated or not, encoded by said DNA sequences.

BACKGROUND OF THE INVENTION

The causative agent of LAS or AIDS, a retrovirus, has been identified by F. BARRE-SINOUSSI et al., Science, 220, 868 (1983). It has the following characteristics. It is T-lymphotropic; its preferred target is constituted by Leu 3 cells (or T4 lymphocytes); it has reverse transcriptase activity necessitating the presence of Mg+ and exhibits strong affinity for poly(adenylate-oligodeoxy-thymidylate) (poly (A)-oligo(dT)12–18). It has a density of 1.16–1.17 in a sucrose gradient, an average diameter of 139 nanometers; and a nucleus having an average diameter of 41 nanometers. Antigens of said virus, particularly a protein p25 are recognized immunologically by antibodies contained in serums taken up from patients afflicted with LAS or AIDS. The p25 protein, which is a core protein, is not recognized immunologically by the p24 protein of the HTLVI and II viruses. The virus is also free of a p19 protein which is immunologically cross-reactive with the p19 proteins of HTLVI and HTLVII.

Retroviruses of this type (sometimes denoted by the generic abbreviation LAV) have been filed in the National Collection of Micro-organism Cultures of the INSTITUT PASTEUR of Paris, under numbers I-232, I-240 and I-241. Virus strains similar to LAV in all respects from the morphological and immunological point of view have been isolated in other laboratories. Reference is made by way of examples to the retrovirus strains named HTLV-III isolated by R. C. GALLO et al., Science, 224, 500 (1984) and by M. G. SARNGADHARAN et al., Science 224, 506 (1984) respectively and to the retrovirus isolated by M. JAY LEVY et al., Science, 225, 840–842 (1984), which virus was designated ARV. For the ease of language the last mentioned viruses, as well as others which have equivalent morphological and immunological properties, will be designated hereafter under the generic designation "LAV". Reference is also made to European patent application filed Sep. 14, 1984, with the priority of British patent application No. 83 24800 filed Sep. 15, 1983 as regards a more detailed description of the LAV retroviruses or the like and of the uses to which extracts of these viruses give rise.

Initially the core antigens were the main antigens of the virus lysates or extracts which were recognized by serums of patients infected with AIDS or LAS, in the test systems which had then been used. A p42 protein, presented as consisting of an envelope protein, had been detected too. In the same manner GALLO et al disclosed a p41 protein which was also deemed to be a possible component of the virus envelope.

Processes for obtaining a LAV virus have also been described. Reference may be made particularly to the article already mentioned of F. BARRE-SINOUSSI et al., as regards the preparation of the virus in T lymphocyte cultures derived either from blood, or from the umbilical cord, or also from bone marrow cells of adult donors in good health. This process comprises particularly the following essential steps:

producing a viral infection of these T lymphocytes, after activation by a lectin mitogen, with a viral suspension derived from a crude supernatant liquor of lymphocytes producing the virus (initially obtained from a patient infected with AIDS or LAS), culturing cells infected with TCGF, in the presence of anti-α-interferon sheep serum, effecting purification of the virus produced (production starts generally between the 9th and the 15th day following infection and lasts from 10 to 15 days), which purification comprises precipitating the virus in polyethylenglycol in order to produce a first concentration of the virus, then centrifugating the preparation obtained in a 20–60% sucrose gradient or in an isotonic gradient of metrizanide (sold under the trade mark NYCODENZ by NYEGAARD, Oslo) and recovering the virus with the band having a density of 1.16–1.17 in the sucrose gradient or of 1.10–1.11 in the NYCO-DENZ gradient.

The LAV virus may also be produced from permanent cell lines of type T, such as the CEM line, or from B lymphoblastoid cell lines, such as obtained by the transformation of the lymphocytes derived from a healthy donor with the Epstein-Barr virus, for instance as disclosed in French patent application Nr. 84 07151 filed May 9, 1984. The permanent cell lines obtained produce continuously a virus (designated as LAV-B in the case of the B lymphoblastoid cell lines) which possesses the essential antigenic and morphological features of the LAV viruses (except that it is collected in a density band sometimes slightly higher than in the preceding case (particularly 1.18) in sucrose. The final purification of the virus can also be carried out in a NYCODENZ gradient.

A method for cloning DNA sequences hybridizable with the genomic RNA of LAS has already been disclosed in British Patent Application Nr. 84 23659 filed on Sep. 19, 1984. Reference is hereafter made to that application as concerns subject matter in common with the further improvements to the invention disclosed herein.

SUMMARY OF THE INVENTION

The invention aims at providing purified unaltered virus forms (or viruses less altered by the purification procedures resorted to) and processes for obtaining said unaltered purified viruses.

The present invention further aims at providing additional new means which should not only be useful for the detection of LAV or related viruses (hereafter more generally referred to as "LAV viruses"), but also have more versatility, particularly in detecting specific parts of the genomic DNA of said viruses whose expression products are not always directly detectable by immunological methods. The present invention further aims at providing polypeptides containing sequences in common with polypeptides comprising antigenic determinants included in the proteins encoded and expressed by the LAV genome occurring in nature. An additional object of the invention is to further provide means for the detection of proteins related to LAV virus, particularly for the diagnosis of AIDS or pre-AIDS or, to the contrary, for the detection of antibodies against the LAV virus or proteins related therewith, particularly in patients afflicted with AIDS or pre-AIDS or more generally in asymptomatic carriers and in blood-related products. Finally the invention also aims at providing immunogenic polypeptides, and more particularly protective polypeptides for use in the preparation of vaccine compositions against AIDS or related syndromes.

The present invention relates to additional DNA fragments, hybridizable with the genomic RNA of LAV as they will be disclosed hereafter, as well as with additional cDNA variants corresponding to the whole genomes of LAV viruses. It further relates to DNA recombinants containing said DNAs or cDNA fragments.

An unaltered purified LAV retrovirus distinguishes from those which have been defined above in that it includes an amount of one or several envelope antigens, sufficient to be visualized when the virus is labeled with $^{35}$S-cysteine, free of unlabeled cysteine in a proportion of 200 microcuries per ml of medium. These antigens, among which particularly glycoproteins, are recognized selectively in vitro by serums of patients affected with SIDA or SLAs or by the serums of asymptomatic carriers of the virus.

A preferred antigen according to the preceding definition obtainable from a lysate of this virus (or by gentle scouring of the envelopes of the virus) is a glycoprotein having a molecular weight of the order of 110,000 daltons, as determined by its migration distance in comparison with the distances of migrations, in a same migration system, of standard proteins having known molecular weights. Particularly comparative measurements were made on a 12.5% polyacrylamide gel under a voltage of 18 V for 18 hours, upon using the following standard proteins (marketed by AMERSHAM):

lysozyme-($^{14}$C)-methyl (MW: 14,300), carbon dioxide-($^{14}$C)-methyl (MW: 30,000), ovalbumin-($^{14}$C)-methyl (MW: 46,000), bovine albumin serum ($^{14}$C)-methyl (MW: 69,000), phosphorylase b-($^{14}$C)-methyl (MW: 92,500), myosine-($^{14}$C)-methyl (MW: 200,000).

The invention relates also to the antigens themselves, particularly that of molecular weight of about 110,000–120,000, which possess also the capability of being recognized by serums of patients infected with AIDS or LAS or by serums of persons who have been exposed to LAV viruses or those analogous with the latter. These antigens have also the characteristic of forming complexes with concanavaline A, said complex being dissociatable in the presence of O-methyl-a-D-mannopyranoside. The antigens according to the invention can also bind to other lectins for example those known under the name "LENTYL-LECTIN". The preferred antigen according to the invention, of molecular weight 110,000, is also sensitive to the action of endoglycosidases. This action is manifested by the production from the antigen of molecular weight 110,000 of a protein having a molecular weight of the order of 90,000, the latter being separable for example by immunoprecipitation or by separation employing the differences in molecular weights (migrations differentiated on gel).

Preferred antigens of the invention are constituted by glycoprotein.

The invention relates also to the process for producing the viruses according to the invention. This process distinguishes essentially from those recalled above at the level of the final purification operation. In particular, the purification step of the process according to the invention is no longer carried out in gradients, but involves the performance of differential centrifugations effected directly on the supernatants of the culture media of the producing cells. These centrifugation operations comprise particularly a first centrifugation at an angular centrifugation velocity, particularly of 10,000 rpm, enabling the removal of nonviral constituents, more particularly of cellular constituents, then a second centrifugation at higher angular velocity, particularly at 45,000 rpm, to obtain the precipitation of the virus itself. In preferred embodiments, the first centrifugation at 10,000 rpm, is maintained for 10 minutes and the second at 45,000 rpm, for 20 minutes. These are, of course, only indicative values, it being understood that it remains within the ability of the specialist to modify the centrifugation conditions, to provide for the separation of the cellular constituents and of the viral constituents.

This modification of the purification process results in the production of viral preparations from which the antigen mentioned can then be isolated more easily, than from virus preparations purified by the previous methods. In any event, the viruses finally obtained by the process of the present invention are more easily recognized by serums of patients or of persons who have been exposed to the LAV virus or to morphologically and antigenically similar strains.

The antigens according to the invention can themselves be obtained from the above disclosed viruses, by lysis (or other suitable processing) of the latter in the presence of any suitable detergent and by recovery and separation of the antigens released. Advantageously, the lysis of the virus is effected in the presence of aprotinin or of any other agent suitable for inhibiting the action of proteases. The separation of the antigens according to the invention can then be carried out by any method known in itself; for example, it is possible to proceed with a separation of the proteins by employing their respectively different migrations in a predetermined gel, the protein sought being then isolated from the zone of the gel in which it would normally be found in an electrophoresis operation under well determined conditions, having regard to its molecular weight. The antigens according to the invention can however be separated from the lysate of the abovesaid viruses, due to their affinity for lectins, in particular concanavaline A or lentyl-lectin. The lectin used is preferably immobilized on a solid support, such as the crosslinked polymer derived from agarose and marketed under the trade mark SEPHAROSE. After washing of the fixed antigens with a suitable buffer, the antigens can be eluted in any suitable manner, particularly by resorting to a O-methyl-α-D mannopyranoside in solution.

A more thorough purification of these antigens can be performed by immunoprecipitation with the serums of patients known to possess antibodies effective against said protein, with concentrated antibody preparations (polyclonal antibodies) or again with monoclonal antibodies, more particularly directed against the antigen according to the invention, in particular that having the molecular weight of 110,000, denoted below by the abbreviation gp 110.

BRIEF DESCRIPTION OF THE DRAWINGS

Additional characteristics of the invention will appear also in the course of the description which follows of the isolation of a virus according to the invention and of antigens, particularly an envelope antigen of the virus. Reference will be made to the drawings in which:

Figure 3A:
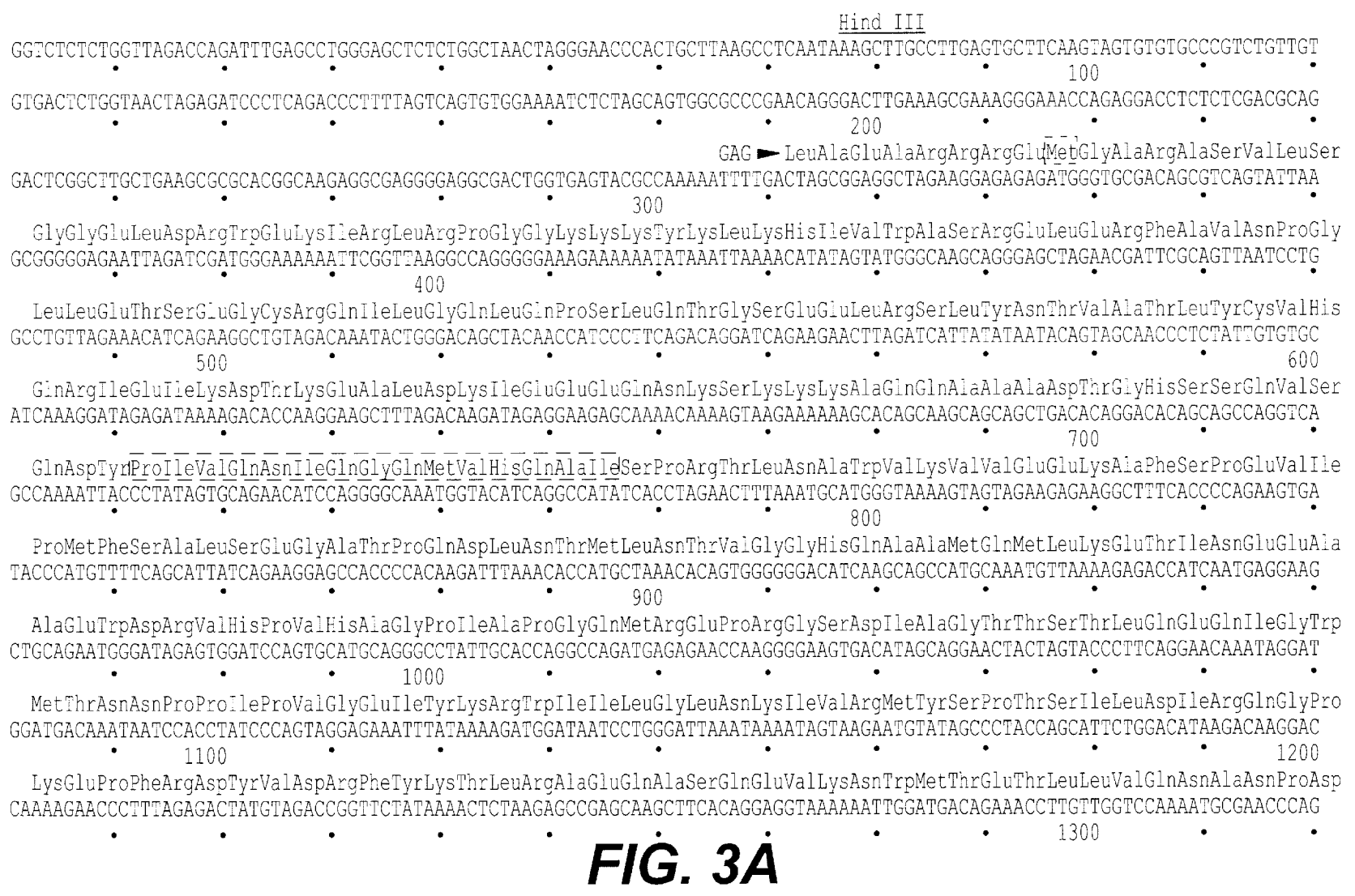
Figure 3C:
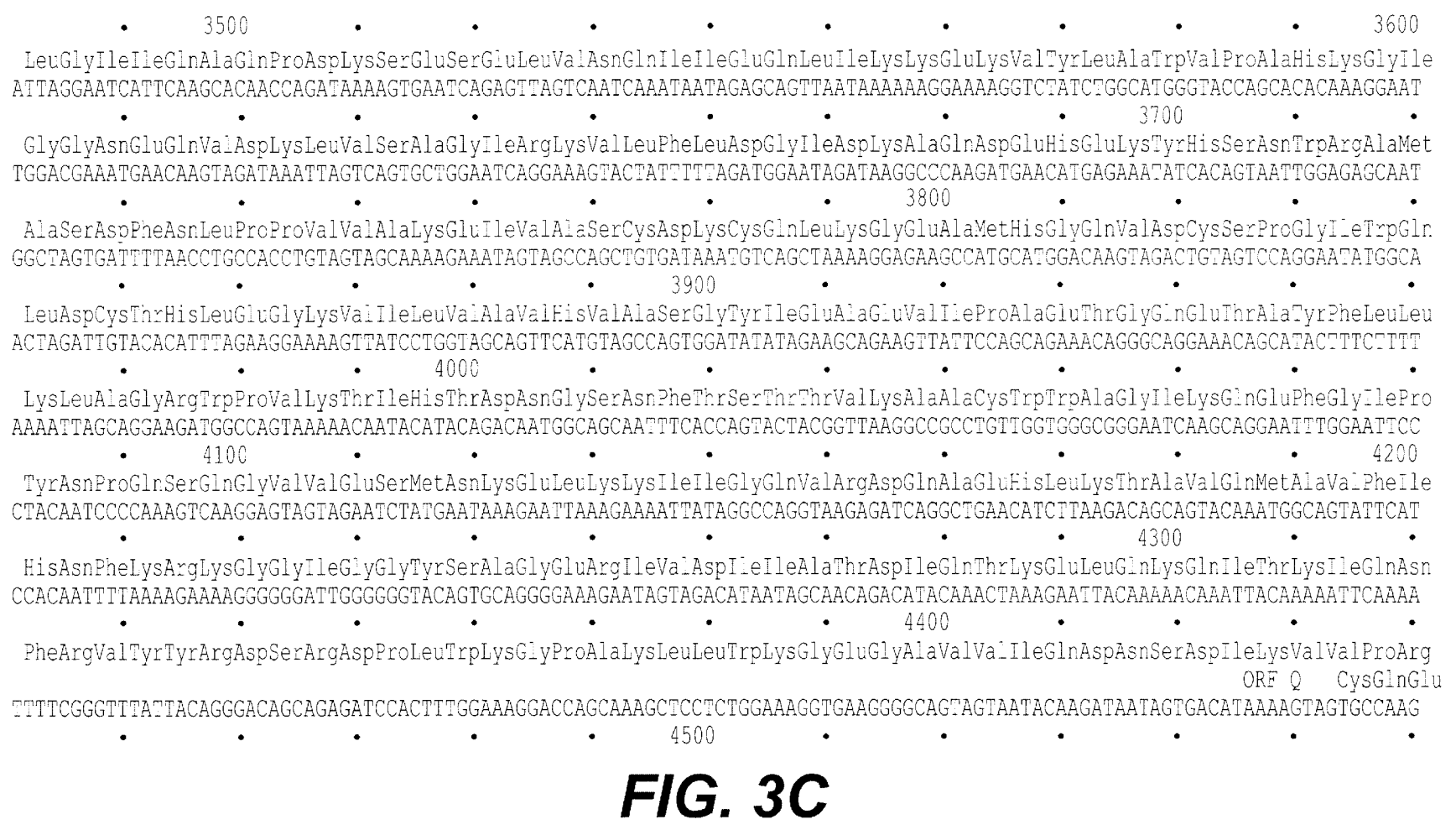
Figure 3C:
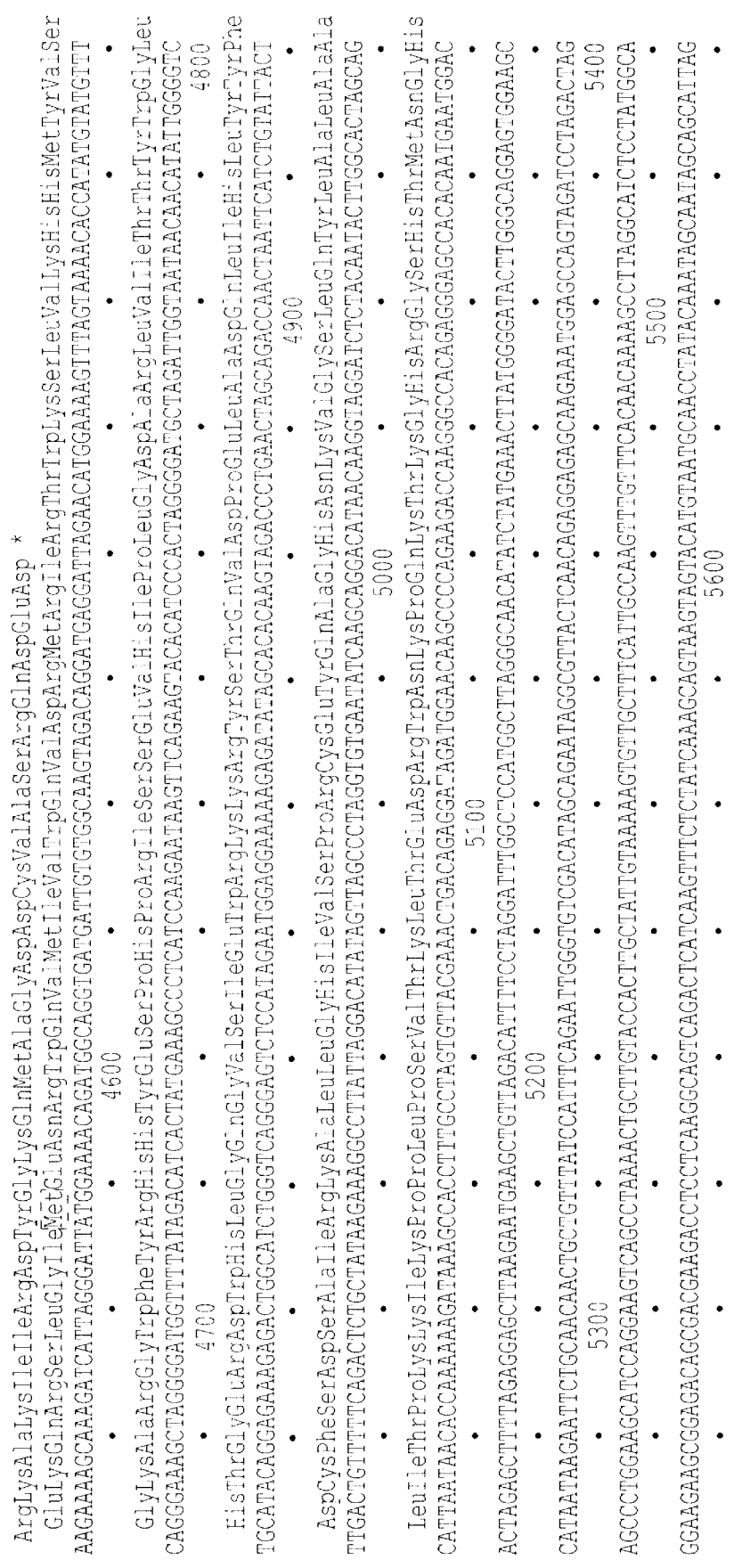
Figure 3D:
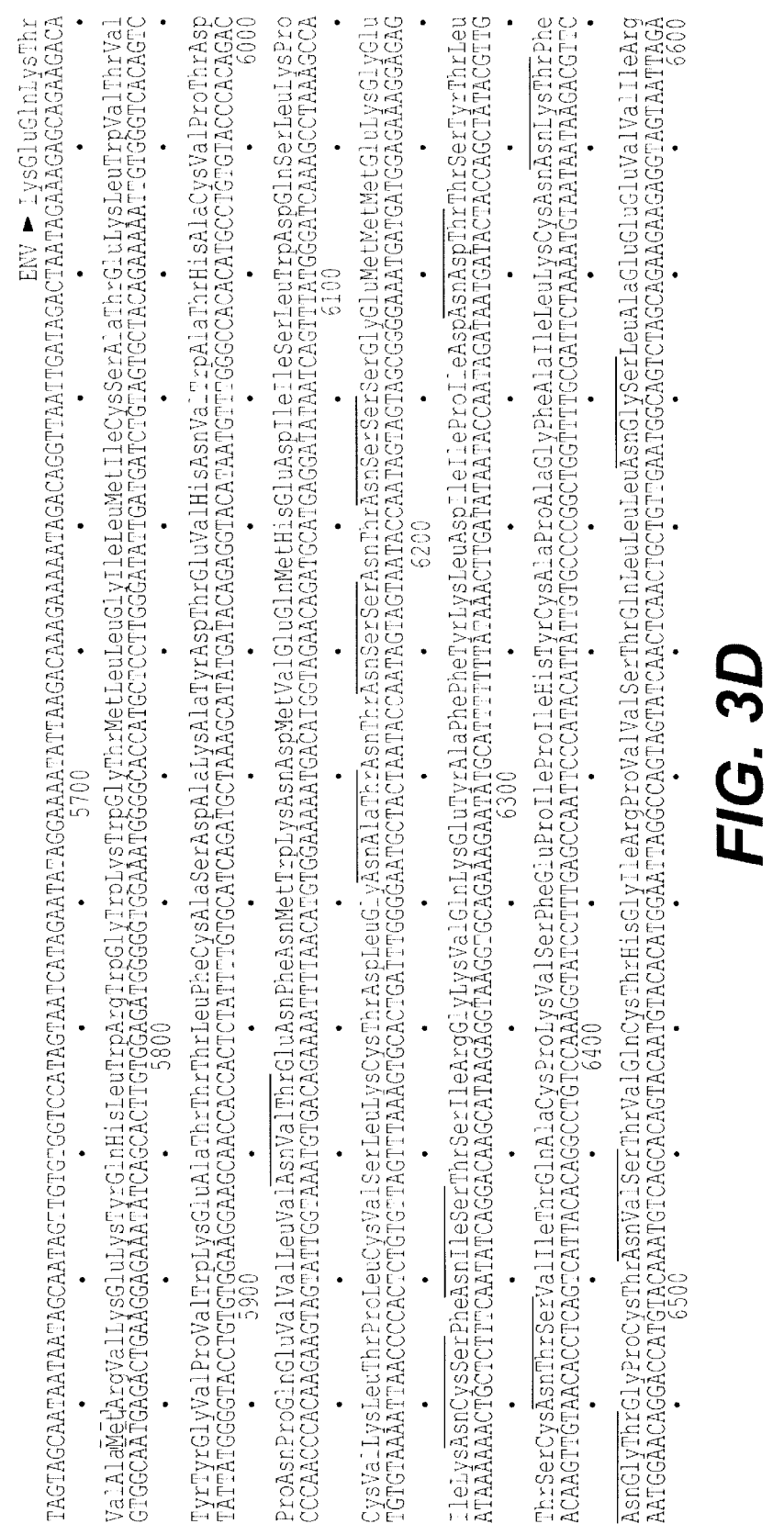
Figure 3D:
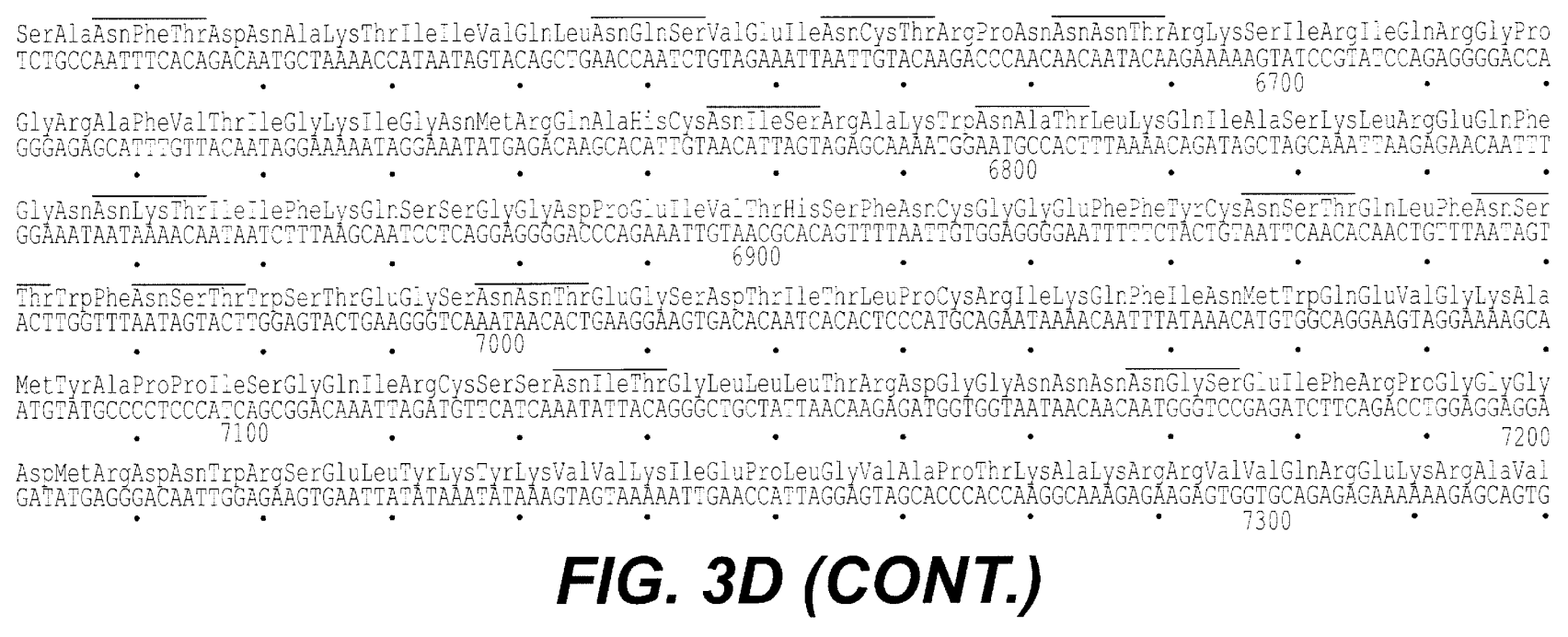

FIG. 3 is the complete sequence of a LAV viral genome.

DETAILED DESCRIPTION OF THE INVENTION

I.—Prodicyion of the Virus and of Antigens

T-lymphocytes derived from a healthy donor and infected with LAV1, under the conditions described by F. BARRE-SINOUSSI et al., on CEM cells derived from a patient afflicted with leukemia and also infected in vitro with LAV1, were kept under cultivation in a medium containing 200 microcuries of $^{35}$S-cysteine and devoid of unlabeled cysteine. The infected lymphocytes were cultured in a non denaturating medium to prevent the degradation of the antigen sought. The supernatant liquor from the culture medium was then subjected to a first centrifugation at 10,000 rpm for 10 minutes to remove the non viral components, then to a second centrifugation at 45,000 rpm for 20 minutes for sedimenting the virus. The virus pellet was then lysed by detergent in the presence of aprotinin (5%) particularly under the conditions described in the article of F. BARRE-SINOUSSI et al.

The same operation was repeated on lymphocytes taken up from a healthy donor as control.

The various lysates were then immuno-precipitated by serums of patients infected with AIDS or with LAS. Serums originating from healthy donors or of donors infected with other diseases were immunoprecipitated too. The media were then subjected to electrophoresis in a SDS-polyacrylamide gel.

Figure 1:
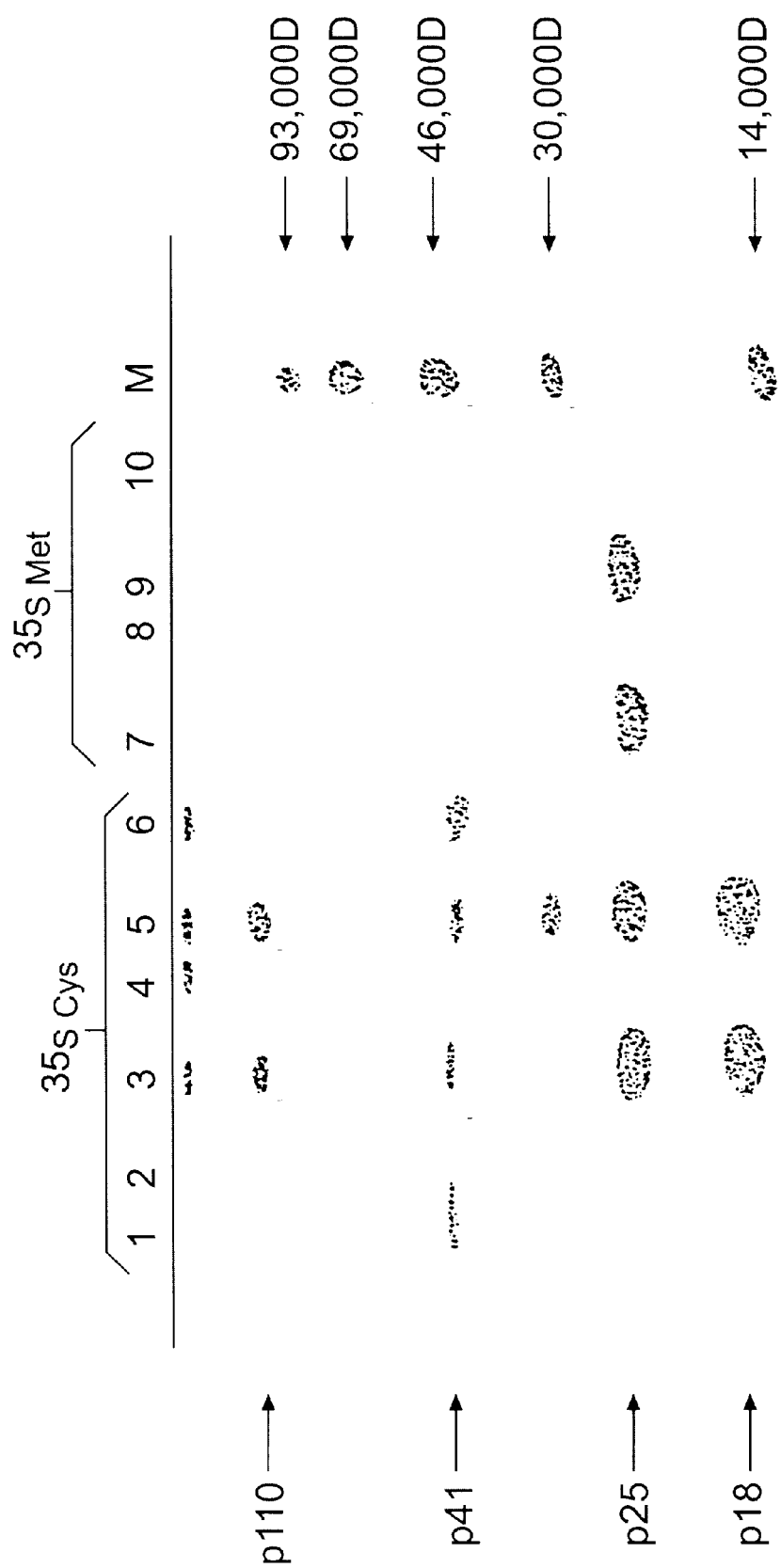
FIG. 1 is derived from a photographic reproduction of gel strips which have been used to carry out electrophoreses of lysate extracts of T lymphocytes, respectively infected and uninfected (controls) by a LAV suspension.

The results are indicated in FIG. 1. The gel strips numbered from 1 to 6 were obtained from preparations labeled by $^{35}$S-cysteine. The strips numbered 7 to 10 show results observed on infected or uninfected lymphocyte preparations labeled with $^{35}$S-methionine. Finally the strip M corresponds to the migration distances of the standard proteins identified above, whose molecular weights are recalled in the right hand portion of the figure.

The references to the labeled viral proteins appear on the left handside of the figure. It is noted that columns 7 to 10 show the specific protein p25 of LAV, labeled with $^{35}$S-methionine. The same protein is absent on strips 8 to 10 corresponding to results obtained with a preparation originating from healthy lymphocytes.

Columns 3 and 5 correspond to the results which have been observed on preparations obtained from lymphocytes infected and labeled with $^{35}$S-cysteine. The proteins p25 and p18, the characteristic core proteins of LAV, and the glycoprotein gp110, also specific of LAV, were also present. Images corresponding to a protein p41 (molecular weight of the order of 41,000) appeared in the various preparations, although less distinctly.

The virus according to the invention and the antigen according to the invention can be either precipitated by lectins, particularly concanavaline A, or fixed to a SEPHAROSE-concanavaline A column. Particularly the purification of the envelope glycoproteins can be carried out as follows. This fixation can particularly be carried out by contacting a lysate of the LAV virus dissolved in a suitable buffer with concanavaline-A bound to SEPHAROSE. A suitable buffer has the following composition:

| Tris | 10 mM |
|---|---|
| NaCl | 0.15 M |
| CaCl$_2$ | 1 mM |
| MgCl$_2$ | 1 mM |

Detergent marketed under the trade mark TRITON 1%

| pH | 7.4 |
|---|---|

When the fixation has been achieved, the SEPHAROSE-concanavaline A is washed with a buffer of the same composition, except that the TRITON concentration is lowered to 0.1%. The elution is then effected with an 0.2 M O-methyl-α-D-mannopyranoside solution in the washing buffer.

The protein may be further concentrated by immuno-precipitation with antibodies contained in the serums of patients infected with AIDS or with polyclonal antibodies obtained from a serum derived from an animal previously immunised against the "unaltered" virus according to the invention or the abovesaid glycoprotein. The protein can then be recovered by dissociation of the complex by a solution having an adequate content of ionic salt. Preferably the antibody preparation is itself immobilised in a manner known in itself on an insoluble support, for instance of the SEPHAROSE B type.

It is also possible to resort to monoclonal antibodies secreted by hybridomas previously prepared against gp 110. These monoclonal antibodies, as well as the hybridomas which produce them, also form part of the invention.

A technique for producing and selecting monoclonal antibodies directed against the gp 110 glycoprotein is described below.

Immunization of the Mice

Groups of Balb/c mice from 6 to 8 weeks old were used. One group receives the virus carrying the abovesaid glycoprotein, another a purified glycoprotein gp 110. The immunization procedure, identical for all mice, comprises injecting 10 mg of the antigenic preparation in the presence of Freund complete adjuvant at day 0, then again but in the presence of Freund incomplete adjuvant at day 14 and without adjuvant at days 28 and 42. The three first injections are made intraperitoneally, the fourth intravenously.

Fusion and Culture of the Hybrids

The non secreting myeloma variant 5.53 P3×63 Ag8, resistant to azaguanine, itself derived from the MOPC-21 cell-line, is used. Fusion with immunised mouse splenocvtes is carried out in the presence of polyethylene-glycol 4000 by the technique of FAZEKAS de st-GROTH and SCHEIDEGGER on the 45th day. The selection of the hybrids in RPMI 16-40 "HAT" medium is carried out in plates having 24 cups (known under the designation COSTAR) by resorting to the same culture techniques.

The hybridomas producing antibodies of adequate specificity are then cloned in plates having 96 cups, in the presence of a "feeder" layer of syngenic thymocytes. The producing clones thus selected are then expanded in 24 cup plates, still in the presence of thymocytes. When the confluence appears in one of the cups, the clone is injected intraperitoneally into a balb/c mouse which had received an injection of PRISTANE 8 days previously and/or kept in liquid culture.

Demonstration of the Anti-LAV Antibodies

Five different techniques enable characterization of the clones producing antibodies of suitable specificity. In a first stage, the hybrids producing antibodies are determined by an ELISA test revealing mouse immunoglobulins in the supernatant liquors. From this first selection, supernatants are sought which have antibodies directed against viral constituents by means of an ELISA test revealing anti-LAV antibodies, or by immunofluorescence on the virus producing human cells. Finally the supernatant liquours are analyzed by radio immunoprecipitation of virus labeled with cysteine and by the Western-Blot technique on viral preparation which permit the determination of the specificities of these anti-LAV antibodies.

Results

Cells obtained from the various fusions are placed under culture in 648 cups. Their microscopic examination shows that the majority of these cups contain a single hybrid clone capable of growing in a "HAT" selective medium. More than 50% among them produce antibodies giving rise to a positive response under ELISA antivirus examination. The most representative fusions are tested by the Western-Blot technique and several of them are subcloned, taking into account their respective specificities reactivities in antivirus ELISA and their behaviours under the culturing conditions. Those hybrids which are more particularly selected are those which produce antibodies which selectively recognise the viral glycoprotein gp110 having a molecular weight of about 110 KD. All the sub clonings give rise to clones producing antibodies which, after expression, are injected into syngenic mice. Analysis of the specificities of the antibodies present in the different ascites liquids confirm the specificity of the antibodies of said ascites with respect to gp110.

The monoclonal antibodies obtained can themselves be employed to purify proteins containing an antigenic site also contained in gp110. The invention relates therefore also to these processes of purification as such. This process is advantageously applied to virus lysates or T lymphocyte lysates or other cells producing LAV or the like, when care has been taken to avoid the uncontrolled separation of gp110 during the purification procedure of the virus, prior to lysis thereof. Needless to say that the process can also be applied to any solution containing gp110 or a protein, polypeptide or glycoprotein comprising an antigenic site normally carried by the envelope protein and recognized by the monoclonal antibody. For practicing this process, the monoclonal antibodies are advantageously immobilized on a solid support, preferably adapted to affinity chromatography operations.

For example, these monoclonal antibodies are fixed to an agarose lattice with three-dimensional cross-linking, marketed under the trade mark SEPHAROSE by the Swedish company PHARMACIA A.G., for example by the cyanogen bromide method.

The invention therefore also relates to a process for separating the antigens concerned, which process comprises contacting a mixture of antigens, including those of interest (for instance a virus lysate or extract), with an affinity column bearing the abovesaid monoclonal antibodies, to selectively fix polypeptides, proteins or glycoproteins selectively recognized by said monoclonal antibodies, recovering the latter by dissociation of the antigen-antibody complex by means of a suitable buffer, particularly a solution of adequate ionic strength, for example of a salt, preferably ammonium acetate (which leaves no residue upon freeze drying of the preparation or a solution acidified to a pH 2–4 or to a glycine buffer at the same pH and recovering the eluted polypeptides, proteins or glycoproteins.

It is self-evident that the invention relates also to polypeptide fragments having lower molecular weights and carrying antigenic sites recognizable by the same monoclonal antibodies. It is clear to the specialist that the availability of monoclonal antibodies recognizing the gp110 glycoprotein gives also access to smaller peptide sequences or fragments containing the common antigenic site or epitope. Fragments of smaller sizes may be obtained by resorting to known techniques. For instance such a method comprises cleaving the original larger polypeptide by enzymes capable of cleaving it at specific sites. By way of examples of such proteins, may be mentioned the enzyme of *Staphylococcus aureus* V8, α-chymotrypsine, "mouse sub-maxillary gland protease" marketed by the BOEHRINGER company, *Vibrio alginolyticus chemovar iophagus* collagenase, which specifically recognizes said peptides Gly-Pro and Gly-Ala, etc.

It is also possible to obtain polypeptides or fragments of envelope antigens of the virus, by cloning fragments excised from a cDNA constructed from genomes of LAV variants.

Figure 2:
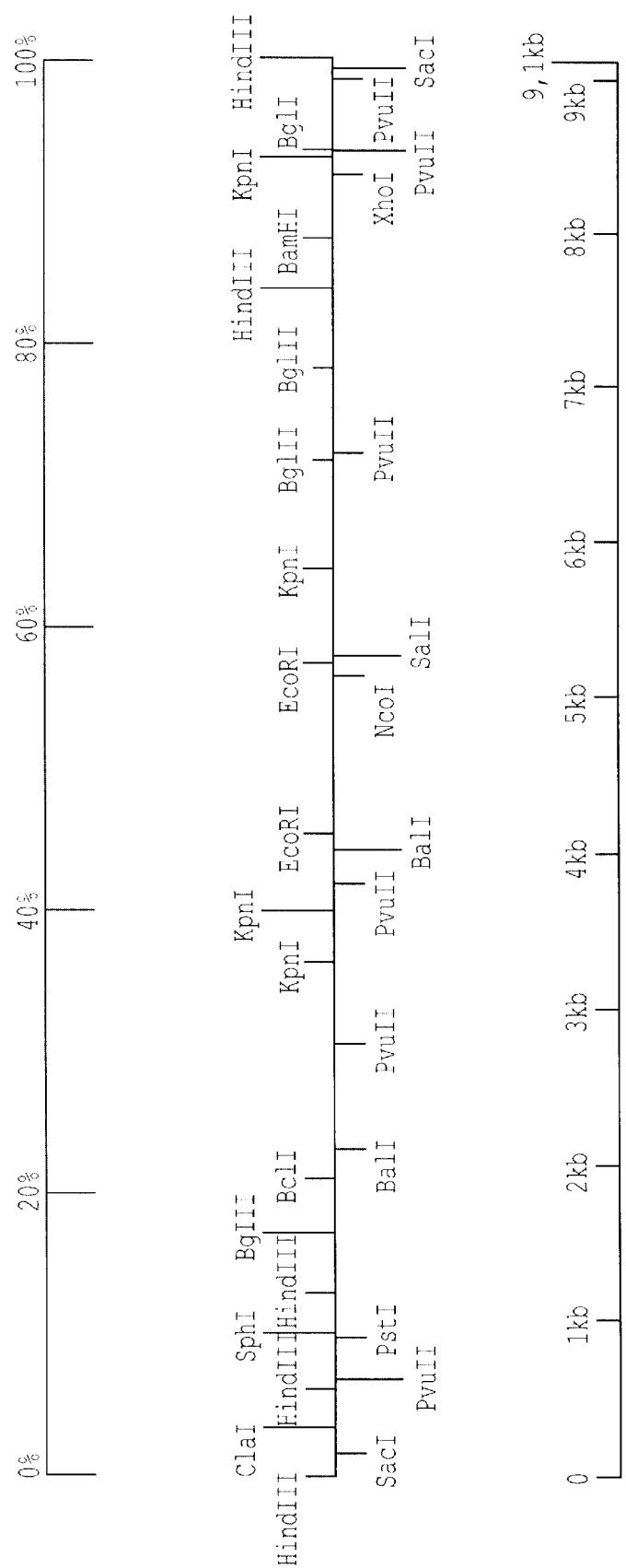
FIG. 2 is the restriction map of a complete LAV genome (clone λJ19).
Figure 6:
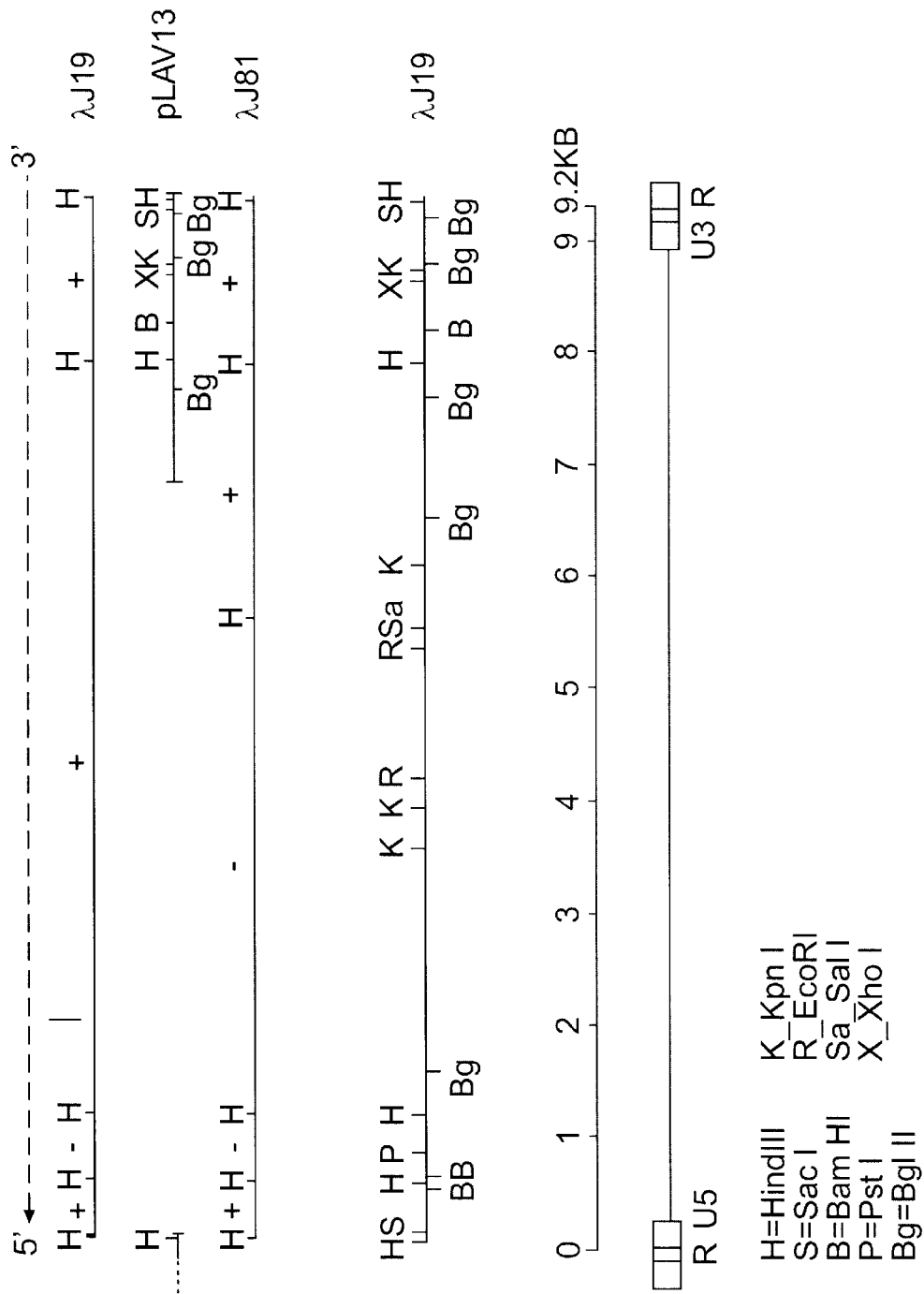
FIG. 6 is a schematic representation of the LAV long terminal repeat (LTR).

FIGS. 2 and 6 are restriction maps of such a cDNA comprising a total of 9.1 to 9.2 kb. The polypeptides coded by cDNA fragments located in the region extending between site KpnI (position 6100) and site BglII (position 9150) of the restriction map of FIG. 2. The presence of a characteristic site of an envelope antigen of the LAV virus or the like in any polypeptide expressed (in a suitable host cell transformed beforehand by a corresponding fragment or by a vector containing said fragment) can be detected by any suitable immunochemical means.

Particularly the invention relates more particularly to polypeptides encoded by cDNA fragments defined hereafter. It also relates to the nucleic acid fragments themselves, including a cDNA variant corresponding to a whole LAV retroviral genome, characterized by a series of restriction sites in the order hereafter (from the 5' end to the 3' end).

The coordinates of the successive sites of the whole LAV genome (see also restriction map of λJ19 in FIG. 2) are indicated hereafter too, with respect to the Hind III site (selected as of coordinate 1) which is located in the R region. The coordinates are estimated with an accuracy of ±200 bp:

| Hind III | 0 |
| Sac I | 50 |
| Hind III | 520 |
| Pst I | 800 |
| Hind III | 1 100 |

-continued

| | |
|---|---|
| Bgl II | 1 500 |
| Kpn I | 3 500 |
| Kpn I | 3 900 |
| Eco RI | 4 100 |
| Eco RI | 5 300 |
| Sal I | 5 500 |
| Kpn I | 6 100 |
| Bgl II | 6 500 |
| Bgl II | 7 600 |
| Hind III | 7 850 |
| Bam HI | 8 150 |
| Xho I | 8 600 |
| Kpn-I | 8 700 |
| Bgl II | 8 750 |
| Bgl II | 9 150 |
| Sac I | 9 200 |
| Hind III | 9 250 |

Another DNA variant according to this invention optionally contains an additional Hind III approximately at the 5 550 coordinate.

Reference is further made to FIG. 2 which shows a more detailed restriction map of said whole-DNA (λJ19).

An even more detailed nucleotidic sequence of a preferred DNA according to the invention is shown in FIG. 3 hereafter.

The invention further relates to other preferred DNA fragments and polypeptide sequences (glycosylated or not glycosylated) which will be referred to hereafter.

Sequencing of LAV

The sequencing and determination of sites of particular interest were carried out on a phage recombinant corresponding to λJ19 disclosed in the abovesaid British Patent application Nr. 84 23659. A method for preparing it is disclosed in that application.

The whole recombinant phage DNA of clone λJ19 (disclosed in the earlier application) was sonicated according to the protocol of DEININGER (1983), Analytical Biochem. 129, 216. The DNA was repaired by a Klenow reaction for 12 hours at 16° C. The DNA was electrophoresed through 0.8% agarose gel and DNA in the size range of 300–600 bp was cut out and electroeluted and precipitated. Resuspended DNA (in 10 mM Tris, pH 8; 0.1 mM EDTA) was ligated into M13mp8 RF DNA (cut by the restriction enzyme SmaI and subsequently alkaline phosphated), using T4 DNA- and RNA-ligases (Maniatis, T. et al. (1982)— Molecular cloning—Cold Spring Harbor Laboratory). An $E.$ $coli$ strain designated as TG1 was used for further study. This strain has the following genotype:

Δlac pro, supE, thi.F' traD36, proAB, lacI$^q$, zΔM15,r$^-$

This $E.$ $coli$ TGI strain has the peculiarity of enabling recombinants to be recognized easily. The blue color of the cells transfected with plasmids which did not recombine with a fragment of LAV DNA is not modified. To the contrary cells transfected by a recombinant plasmid containing a LAV DNA fragment yield white colonies. The technique which was used is disclosed in Gene (1983), 26, 101.

This strain was transformed with the ligation mix using the Hanahan method (Hanahan D (1983) J. Mol. Biol. 166, 557). Cells were plated out on tryptone-agarose plate with IPTG and X-gal in soft agarose. White plaques were either picked and screened or screened directly in situ using nitrocellulose filters. Their DNAs were hybridized with nick-translated DNA inserts of pUC18 Hind III subclones of λJ19. This permitted the isolation of the plasmids or subclones of λ which are identified in the table hereafter. In relation to this table it should also be noted that the designation of each plasmid is followed by the deposition number of a cell culture of $E.$ $coli$ TGI containing the corresponding plasmid at the "Collection Nationale des Cultures de Microorganismes" (C.N.C.M.) of the Pasteur Institute in Paris, France. A non-transformed TGI cell line was also deposited at the C.N.C.M. under Nr. I-364. All these deposits took place on Nov. 15, 1984. The sizes of the corresponding inserts derived from the LAV genome have also been indicated.

TABLE

Essential features of the recombinant plasmids

| | | |
|---|---|---|
| - pJ19 - 1 plasmid | (I-365) | 0.5 kb |
| Hind III - Sac I - Hind III | | |
| - pJ19 - 17 plasmid | (I-367) | 0.6 kb |
| Hind III - Pst 1 - Hind III | | |
| - pJ19 - 6 plasmid | (I-366) | 1.5 kb |
| Hind III (5') | | |
| Bam HI | | |
| Xho I | | |
| Kpn I | | |
| Bgl II | | |
| Sac I (3') | | |
| Hind III | | |
| - pJ19-13 plasmid | (I-368) | 6.7 kb |
| Hind III (5') | | |
| Bgl II | | |
| Kpn I | | |
| Eco RI | | |
| Eco RI | | |
| Sal I | | |
| Kpn I | | |
| Bgl II | | |
| Bgl II | | |
| Hind III (3') | | |

Positively hybridizing M13 phage plates were grown up for 5 hours and the single-stranded DNAs were extracted.

M13mp8 subclones of λJ19 DNAs were sequenced according to the dideoxy method and technology devised by Sanger et al. (Sanger et al. (1977), Proc. Natl. Acad. Sci. USA, 74, 5463 and M13 cloning and sequencing handbook, AMERSHAM (1983). The 17-mer oligonucleotide primer α-$^{35}$SdATP (400 Ci/mmol, AMERSHAM), and 0.5×–5× buffer gradient gels (Biggen M.D. et al (1983, Proc. Nati. Acad. Sci. USA, 50, 3963) were used. Gels were read and put into the computer under the programs of Staden (Staden R. (1982), Nucl. Acids Res. 10 4731). All the appropriate references and methods can be found in the AMERSHAM M13 cloning and sequencing handbook.

The complete DNA sequence of λJ19 (also designated as LAV-Ia) is shown in FIG. 3

The sequence was reconstructed from the sequence of phage λJ19 insert. The numbering starts at the cap site which was located experimentally (see hereafter). Important genetic elements, major open reading frames and their predicted products are indicated together with the HindIII cloning sites. The potential glycosylation sites in the env gene are overlined. The NH$_2$-terminal sequence of p25$^{gag}$ determined by protein microsequencing is boxed.

Each nucleotide was sequenced on average 5.3 times: 85% of the sequence was determined on both strands and the remainder sequenced at least twice from independent clones. The base composition is T, 22.2%; C, 17.8%; A, 35.8%; G, 24.2%; G+C, 42%. The dinucleotide GC is greatly under represented (0.9%) as common amongst eukaryotic sequences (Bird 1980).

Figure 4:
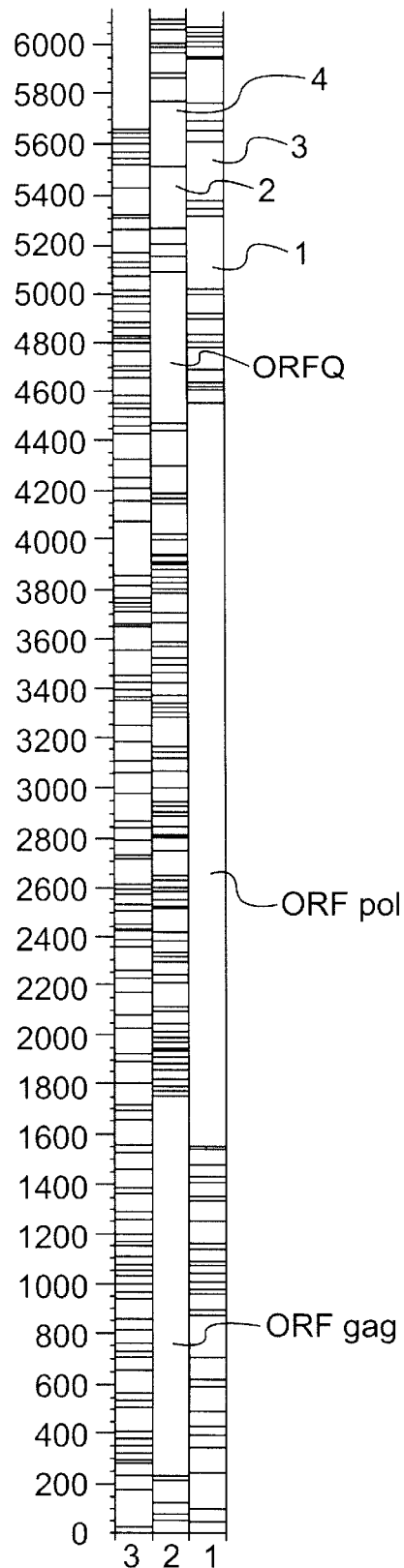
FIGS. 4 and 5 show diagrammatically parts of the three possible reading phases of LAV genomic RNA, including the open reading frames (ORF) apparent in each of said reading phases.
Figure 5:
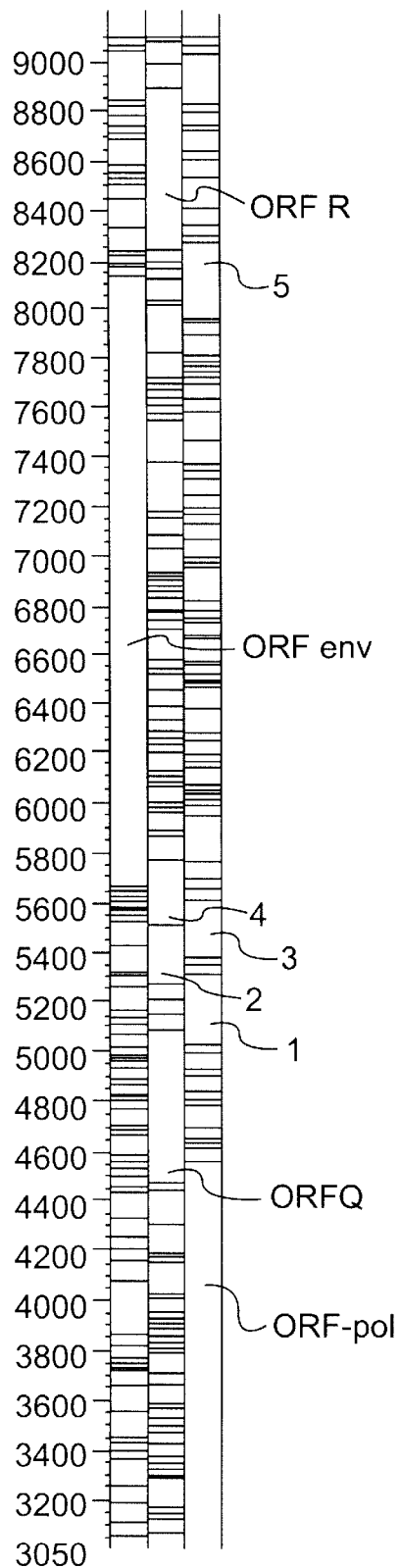

FIGS. 4 and 5 provide a diagram atized representation of the lengths of the successive open reading frames corresponding to the successive reading phases (also referred to by numbers "1", "2" and "3" appearing in the left handside part of FIG. 4). The relative positions of these open reading frames (ORF) with respect to the nucleotidic structure of the LAV genome is referred to by the scale of numbers representative of the respective positions of the corresponding nucleotides in the DNA sequence. The vertical bars correspond to the positions of the corresponding stop codons.

The following genes and DNA fragments can be distinguished on the different reading frames shown. Reference is then also made to the proteins or glycoproteins encoded by said genes and fragments.

1) The "gag gene" (or ORF-gag)

The "gag gene" codes for core proteins.

gag: near the 5' extremity of the gag orf is a "typical" initiation codon (Kozak 1984) (position 336) which is not only the first in the gag orf, but the first from the cap site. The precursor protein is 500-amino acids long. Calculated MW=55841 agrees with the 55 kd gag precursor polypeptide. The N-terminal amino acid sequence of the major core protein p25 is encoded by the nucleotide sequence starting from position 732 (FIG. 3). This formally makes the link between the cloned LAV genome and the immunologically characterized LAV p25 protein. The protein encoded 5' of the p25 coding sequence is rather hydrophilic. Its calculated MW of 14866 is consistent with that of the gag protein p18. The 3' part of the gag region codes probably for the retroviral nucleic acid binding protein (NBP). Indeed, like in HTLV-1 (Seiki et al., 1983) and RSV (Schwartz et al., 1983), the motif $Cys-X_2-Cys-X_{8-9}-Cys$ common to all NBP (Orozlan et al., 1984) is found duplicated (nucleotides 1509 and 1572 in LAV sequence). Consistent with its function the putative NBP is extremely basic (17% Arg+Lys).

Particularly it appears that a genomic fragment (ORF-gag) thought to code for the core antigens including the p25, p18 and p13 proteins is located between nucleotidic position 312 (starting with 5' CTA GCG GAG-3') and nucleotidic position 1835 (ending by CTCG TCA CAA 3'). The structure of the peptides or proteins encoded by parts of said ORF is deemed to be that corresponding to phase 2.

The methionine aminoacid "M" coded by the ATG at position 336–338 is the probable initiation methionine of the gag protein precursor. The end of ORF-gag and accordingly of gag protein appears to be located at position 1835.

The beginning of p25 protein, thought to start by a Pro-Ile-Val-Gln-Asn-Ile-Gln-Gly-Gln-Met-Val-His . . . aminoacid sequence is thought to be coded for by the nucleotidic sequence CCTATA . . . , starting at position 732.

The invention is thus more particularly concerned with and relates to the DNA sequence, extending from nucleotide 336 up to about nucleotide 1650, deemed to encode a p55 protein which is considered a containing amino acid sequences corresponding to those of the core proteins p18 and p25 of the LAV virus;

the DNA sequence, extending from nucleotide 732 up to about nucleotide 1300, deemed to encode the p25 protein;

the DNA sequence, extending from about nucleotide 1371 to about nucleotide 1650, deemed to encode the p13 protein;

the DNA sequence, extending from nucleotide 336 up to about nucleotide 611, deemed to encode the p18 protein;

The invention also relates to the purified polypeptides which have the amino acid structures encoded by the abovesaid fragments, particularly the p13, p18, p25, p55 proteins or polypeptides which have the structures corresponding to those resulting from the direct transitions of the DNA sequences or fragments which have been defined more specifically hereabove, which peptidic sequences flow directly from FIG. 3. More particularly the invention relates to purified polypeptides having peptidic sequences identical or equivalent to those encoded by the DNA sequences extending from the following nucleotide positions 336 to 1650 (p55)
336 to 611 (p18)
1371 to 1650 (p13)
732 to 1300 (p25).

It should be mentioned that the p13, p18 and p25 all appear to derive from a same precursor, i.e. p55.

The invention further concerns polypeptide fragments encoded by corresponding DNA fragments of the gag open reading frame. Particularly hydrophilic peptides in the gag open reading frame are identified hereafter. They are defined starting from aminoacid 1=Met coded by the ATG starting from 336=338 in the LAV DNA sequence (FIG. 3) and then further numbered in accordance with their order in the gag sequence. The first and second numbers in relation to each peptide refer to the respective N-terminal and C-terminal-amino acid respectively.

Those hydrophilic peptides include:

amino acids 12–32 inclusive, i.e. Glu-Leu-Asp-Arg-Trp-Glu-Lys-Ile-Arg-Leu-Arg-Pro-Gly-Gly-Lys-Lys-Lys-Tyr-Lys-Leu-Lys aminoacids 37–46 inclusive, i.e. Ala-Sr-Arg-Glu-Leu-Glu-Arg-Phe-Ala-Valaminoacids 49–79 inclusive, i.e. Gly-Leu-Leu-Glu-Thr-Ser-Glu-Gly-Cys-Arg-Gln-Ile-Leu-Gly-Gln-Leu-Gln-Pro-Ser-Leu-Gln-Thr-Gly-Ser-Glu-Glu-Leu-Arg-Ser-Leu-Tyraminoacids 88–153 inclusive, i.e. Val-His-Gln-Arg-Ile-Glu-Ile-Lys-Asp-Thr-Lys-Glu-Ala-Leu-Asp-Lys-Ile-Glu-Glu-Glu-Gln-Asn-Lys-Ser-Lys-Lys-Lys-Ala-Gln-Gln-Ala-Ala-Ala-Asp-Thr-Gly-His-Ser-Ser-Gln-Val-Ser-Gln-Asn-Tyr-Pro-Ile-Val-Gln-Asn-Ile-Gln-Gly-Gln-Met-Val-His-Gln-Ala-Ile-Ser-Pro-Arg-Thr-Leu-Asnaminoacids 158–165 inclusive, i.e. Val-Val-Glu-Glu-Lys-Ala-Phe-Seraminoacids 178–188 inclusive, i.e. Gly-Ala-Thr-Pro-Gln-Asp-Leu-Asn-Thr-Met-Leuaminoacids 200–220 inclusive, i.e. Met-Leu-Lys-Glu-Thr-Ile-Asn-Glu-Glu-Ala-Ala-Glu-Trp-Asp-Arg-Val-His-Pro-Val-His-Alaaminoacids 226–234 inclusive, i.e. Gly-Gln-Met-Arg-Glu-Pro-Arg-Gly-Seraminoacids 239–264 inclusive, i.e. Thr-Thr-Ser-Thr-Leu-Gln-Glu-Gln-Ile-Gly-Trp-Met-Thr-Asn-Asn-Pro-Pro-Ile-Pro-Val-Gly-Glu-Ile-Tyr-Lys-Argaminoacids 288–331 inclusive, i.e. Gly-Pro-Lys-Glu-Pro-Phe-Arg-Asp-Tyr-Val-Asp-Arg-Phe-Tyr-Lys-Thr-Leu-Arg-Ala-Glu-Gln-Ala-Ser-Gln-Glu-Val-Lys-Asn-Trp-Met-Thr-Glu-Thr-Leu-Leu-Val-Gln-Asn-Ala-Asn-Pro-Asp-Cys-Lysaminoacids 352–361 inclusive, i.e. Gly-Val-Gly-Gly-Pro-Gly-His-Lys-Ala-Argaminoacids 377–390 inclusive, i.e. Met-Met-Gln-Arg-Gly-Asn-Phe-Arg-Asn-Gln-Arg-Lys-Ile-Valaminoacids 399–432 inclusive, i.e. Gly-His-Ile-Ala-Arg-Asn-Cys-Arg-Ala-Pro-Arg-Lys-Lys-Gly-Cys-Trp-Lys-Cys-Gly-Lys-Glu-Gly-His-Gln-Met-Lys-Asp-Cys-Thr-Glu-Arg-Gln-Ala-Asnaminoacids 437–484 inclusive, i.e. Ile-Trp-Pro-Ser-Tyr-Lys-Gly-Arg-Pro-Gly-Asn-Phe-Leu-Gln-Ser-Arg-Pro-Glu-Pro-Thr-Ala-Pro-Pro-Glu-Glu-Ser-Phe-Arg-Ser-Gly-Val-Glu-Thr-Thr-Thr-Pro-Ser-Gln-Lys-Gln-Glu-Pro-Ile-Asp-Lys-Glu-Leu-Tyraminoacids 492–498 inclusive, i.e. Leu-Phe-Gly-Asn-Asp-Pro-Ser The invention also relates to any combination of these peptides.

2) The "pol gene" (or ORF-pol)

Pol: The reverse transcriptase gene can encode a protein of up to 1,003 aminoacids (calculated MW=113629). Since the first methionine codon is 92 triplets from the origin of the open reading frame, it is possible that the protein is translated from a spliced messenger RNA, so giving a gag-pol polyprotein precursor.

The pol coding region is the only one in which significant homology has been found with other retroviral protein sequences, three domains of homology being apparent. The first is a very short region of 17 aminoacids (starting at 1856). Homologous regions are located within the p15 gag$^{RSV}$ protease (Dittmar and Moelling 1978) and a polypeptide encoded by an open reading frame located between gag and pol of HTLV-1 (FIG. 4) (Schwartz et al., 1983, Seiki et al., 1983). This first domain could thus correspond to a conserved sequence in viral proteases. Its different location within the three genomes may not be significant since retroviruses, by splicing or other mechanisms express a gag pol polyprotein precursor (Schwartz et al., 1983, Seiki et al., 1983). The second and most extensive region of homology (starting at 2048) probably represents the core sequence of the reverse transcriptase. Over a region of 250 aminoacids, with only minimal insertions or deletions, LAV shows 38% aminoacid identity with RSV, 25% with HTLV-I, 21% with MoMuLV(Schinnick et al., 1981) while HTLV-I and RSV show 38% identity in the same region. A third homologous region is situated at the 3end of the pol reading frame and corresponds to part of the pp32 peptide of RSV that has exonuclease activity (Misra et al., 1982). Once again, there is greater homology with the corresponding RSV sequence than with HTLV-1.

FIG. 3 also shows that the DNA fragment extending from nucleotidic position 1631 (starting with 5'TTT TTT . . . 3' to nucleotidic position 5162 thought to correspond to the pol gene. The polypeptidic structure of the corresponding polypeptides is deemed to be that corresponding to phase 1. It stops at position 4639 (end by 5 'G GAT GAG GAT 3').

These genes are thought to code for the virus polymerase or reverse transcriptase.

3) The Envelope Gene (or ORF-env)

env: The env open reading frame has a possible initiator methionine codon very near the beginning (8th triplet). If so the molecular weight of the presumed env precursor protein (861 aminoacids, MWcalc=97376) is consistent with the size of the LAV glycoprotein (110 kd and 90 kd after glycosidase treatment). There are 32 potential N-glycosylation sites (Asn-X-Ser/Thr) which are overlined in FIG. 3. An interesting feature of env is the very high number of Trp residues at both ends of the protein.

The DNA sequence thought to code for envelope proteins is thought to extend from nucleotidic position 5746 (starting with 5'AAA GAG GAG A . . . 3') up to nucleotidic position 8908 (ending by . . . A ACT AAA GAA 3'). Polypeptidic structures of sequences of the envelope protein correspond to those read according to the "phase 3" reading phase.

The start of env transcription is thought to be at the level of the ATG codon at position 5767–5769.

There are three hydrophobic regions, characteristic of the retroviral envelope proteins (Seiki et al., 1983) corresponding to a signal peptide (encoded by nucleotides 5815-5850 bp), a second region (7315–7350 bp) and a transmembrane segment (7831–7890 bp). The second hydrophobic region (7315–7350 bp) is preceded by a stretch rich in Arg+Lys. It is possible that this represents a site of proteolytic cleavage, which by analogy with over retroviral proteins, would give an external envelope polypeptide and a membrane associated protein (Seiki et al., 1983, Kiyokawa et al., 1984). A striking feature of the LAV envelope protein sequence is that the segment encoding the transmembrane protein is of unusual length (150 residues). The env protein shows no homology to any sequence in protein data banks. The small aminoacid motif common to the transmembrane proteins of all leukemogenic retroviruses (Cianciolo et al., 1984) is not present in lav env.

The invention concerns more particularly the DNA sequence extending from nucleotide 5746 (starting of the reading phase), particularly 5767 (starting of the translation) up to nucleotide 8439 deemed to encode the gp 110 (envelope glycoprotein of the LAV virus which has a molecular weight of about 110,000 daltons) beginning at about nucleotide as well as the polypeptidic backbone of the glycoprotein sequence which corresponds to that having an approximate molecular weight which was initially believed to be 90,000 daltons, and which turned out to be 55,000. The polypeptide resulting from the complete removal of sugar residues of gp 110 can be obtained by the treatment of said gp 110 with the appropriate glycosidase.

The invention further relates to the purified polypeptides which have the aminoacid structure (or polypeptidic backbone) of the gp110 and gp90, which correspond to the direct translation of the DNA sequences and fragments which have been defined more specifically hereabove (FIG. 3).

The invention further relates to polypeptides containing neutralizing epitopes.

The locations of neutralizing epitopes are further apparent in FIG. 3. Reference is more particularly made to the overlined groups of three letters included in the aminoacid sequences of the envelope proteins (reading phase 3) which can be designated generally by the formula Asn-X-Ser or Asn-X-Thr, wherein X is any other possible aminoacid. Thus the initial protein product or polypeptide backbone of the env glycoprotein has a molecular weight in excess of 91,000. These groups are deemed to generally carry glycosylated groups. These Asn-X-Ser and Asn-X-Thr groups with attached glycosylated groups form together hydrophilic regions of the protein and are deemed to be located at the periphery of and to be exposed outwardly with respect to the normal conformation of the proteins. Consequently they are considered as being epitopes which can efficiently be brought into play in vaccine compositions.

The invention thus concerns with more particularity peptide sequences included in the env-proteins and excizable therefrom (or having the same aminoacid structure), having sizes not exceeding 200 aminoacids.

Preferred peptides of this invention (referred to hereafter as a, b, c, d, e, f) are deemed to correspond to those encoded by the nucleotide sequences which extend respectively between the following positions a) from about 6171 to about 6276
b) from about 6336 to about 6386
c) from about 6466 to about 6516
d) from about 6561 to about 6696
e) from about 6936 to about 7006 f) from about 7611 to about 7746

Other hydrophilic peptides in the env open reading frame are identified hereafter. They are defined starting from aminoacid 1=lysine coded by the AAA at position 5746–5748 in the LAV DNA sequence (FIG. 3) and then further numbered in accordance with their order with respect to the end sequence. The first and second numbers in relation to each peptide refer to their respective N-terminal and C-terminal aminoacids.

These hydrophilic peptides are:

aminoacids 8–23 inclusive, i.e. Met-Arg-Val-Lys-Glu-Lys-Tyr-Gln-His-Leu-Trp-Arg-Trp-Gly-Trp-Lysaminoacids 63–78 inclusive, i.e. Ser-Asp-Ala-Lys-Ala-Tyr-Asp-Thr-Glu-Val-His-Asn-Val-Trp-Ala-Thraminoacids 82–90 inclusive, i.e. Val-Pro-Thr-Asp-Pro-Asn-Pro-Gln-Gluaminoacids 97–123 inclusive, i.e. Thr-Glu-Asn-Phe-Asn-Met-Trp-Lys-Asn-Asp-Met-Val-Glu-Gln-Met-His-Glu-Asp-Ile-Ile-Ser-Leu-Trp-Asp-Gln-Ser-Leuaminoacids 127–183 inclusive, i.e. Val-Lys-Leu-Thr-Pro-Leu-Cys-Val-Ser-Leu-Lys-Cys-Thr-Asp-Leu-Gly-Asn-Ala-Thr-Asn-Thr-Asn-Ser-Ser-Asn-Thr-Asn-Ser-Ser-Ser-Gly-Glu-Met-Met-Met-Glu-Lys-Gly-Glu-Ile-Lys-Asn-Cys-Ser-Phe-Asn-Ile-Ser-Thr-Ser-Ile-Arg-Gly-Lys-Val-Gln-Lysaminoacids 197–201 inclusive, i.e. Leu-Asp-Ile-Ile-Pro-Ile-Asp-Asn-Asp-Thr-Thraminoacids 239–294 inclusive, i.e. Lys-Cys-Asn-Asn-Lys-Thr-Phe-Asn-Gly-Thr-Gly-Pro-Cys-Thr-Asn-Val-Ser-Thr-Val-Gln-Cys-Thr-His-Gly-Ile-Arg-Pro-Val-Val-Ser-Thr-Gln-Leu-Leu-Leu-Asn-Gly-Ser-Leu-Ala-Glu-Glu-Glu-Val-Val-Ile-Arg-Ser-Ala-Asn-Phe-Thr-Asp-Asn-Ala-Lysaminoacids 300–327 inclusive, i.e. Leu-Asn-Gln-Ser-Val-Glu-Ile-Asn-Cys-Thr-Arg-Pro-Asn-Asn-Asn-Thr-Arg-Lys-Ser-Ile-Arg-Ile-Gln-Arg-Gly-Pro-Gly-Argaminoacids 334–381 inclusive, i.e. Lys-Ile-Gly-Asn-Met-Arg-Gln-Ala-His-Cys-Asn-Ile-Ser-Arg-Ala-Lys-Trp-Asn-Ala-Thr-Leu-Lys-Gln-Ile-Ala-Ser-Lys-Leu-Arg-Glu-Gln-Phe-Gly-Asn-Asn-Lys-Thr-Ile-Ile-Phe-Lys-Gln-Ser-Ser-Gly-Gly-Asp-Proaminoacids 397–424 inclusive, i.e. Cys-Asn-Ser-Thr-Gln-Leu-Phe-Asn-Ser-Thr-Trp-Phe-Asn-Ser-Thr-Trp-Ser-Thr-Glu-Gly-Ser-Asn-Asn-Thr-Glu-Gly-Ser-Aspaminoacids 466–500 inclusive, i.e. Leu-Thr-Arg-Asp-Gly-Gly-Asn-Asn-Asn-Asn-Gly-Ser-Glu-Ile-Phe-Arg-Pro-Gly-Gly-Gly-Asp-Met-Arg-Asp-Asn-Trp-Arg-Ser-Glu-Leu-Tyr-Lys-Tyr-Lys-Valaminoacids 510–523 inclusive, i.e. Pro-Thr-Lys-Ala-Lys-Arg-Arg-Val-Val-Gln-Arg-Glu-Lys-Argaminoacids 551–577 inclusive, i.e. Val-Gln-Ala-Arg-Gln-Leu-Leu-Ser-Gly-Ile-Val-Gln-Gln-Gln-Asn-Asn-Leu-Leu-Arg-Ala-Ile-Glu-Ala-Gln-Gln-His-Leuaminoacids 594–603 inclusive, i.e. Ala-Val-Glu-Arg-Tyr-Leu-Lys-Asp-Gln-Gln aminoacids 621–630 inclusive, i.e. Pro-Trp-Asn-Ala-Ser-Trp-Ser-Asn-Lys-Seraminoacids 657–679 inclusive, i.e. Leu-Ile-Glu-Glu-Ser-Gln-Asn-Gln-Gln-Glu-Lys-Asn-Glu-Gln-Glu-Leu-Leu-Glu-Leu-Asp-Lys-Trp-Alaaminoacids 719–758 inclusive, i.e. Arg-Val-Arg-Gln-Gly-Tyr-Ser-Pro-Leu-Ser-Phe-Gln-Thr-His-Leu-Pro-Thr-Pro-Arg-Gly-Pro-Asp-Arg-Pro-Glu-Gly-Ile-Glu-Glu-Glu-Gly-Gly-Glu- Arg-Asp-Arg-Asp-Arg-Ser-Ileaminoacids 780–803 inclusive, i.e. Tyr-His-Arg-Leu-Arg-Asp-Leu-Leu-Leu-Ile-Val-Thr-Arg-Ile-Val-Glu-Leu-Leu-Gly-Arg-Arg-Gly-Trp-Glu- The invention also relates to any combination of these peptides.

4) The Other ORFs

The invention further concerns DNA sequences which provide open reading frames defined as ORF-O, ORF-R and as "1", "2", "3", "4", "5", the relative positions of which appear more particularly in FIGS. 3 and 5.

These ORFs have the following locations:

| ORF-O | phase | 1 | start | 4554 | stop | 5162 |
|---|---|---|---|---|---|---|
| ORF-R | " | 2 | " | 8325 | " | 8972 |
| ORF-1 | " | 1 | " | 5105 | " | 5392 |
| ORF-2 | " | 2 | " | 5349 | " | 5591 |
| ORF-3 | " | 1 | " | 5459 | " | 5692 |
| ORF-4 | " | 2 | " | 5595 | " | 5849 |
| ORF-5 | " | 1 | " | 8042 | " | 8355 |

ORFs O and F

The viral (+) strand of the LAV genome was found to contain the statutory retroviral genes encoding the core structural proteins (gag), reverse transcriptase (pol) and envelope protein (env), and two extra open reading frames (orf) which we call O and F (Table 1). The genetic organization of LAV, 5'LTR-gag-pol-Q-env-F-3'LTR, is unique. Whereas in all replication competent retroviruses pol and env genes overlap, in LAV they are separated by orf O (192 amino acids) followed by four small (<100 triplets) orf. The orf F (206 amino acids) slightly overlaps the 3' end of env and is remarkable in that it is half encoded by the U3 region of the LTR.

Such a structure places LAV clearly apart from previously sequenced retroviruses (FIG. 6). the (−) strand is apparently non coding. The additional HindIII site of the LAV clone λJ81 (with respect to λJ19) maps to the apparently non-coding region between O and env (positions 5166-5745). Starting at position 5501 is a sequence (AAGCCT) which differs by a single base (underlined) from the HindIII recognition sequence. It is to be anticipated that many of the restriction site polymorphism between different isolates will map to this region. Clone λJ81 has also been referred to in British application Nr. 84 23659 filed on Sep. 15, 1984.

O and F

The nucleotide positions of their respective extremities are given in Table 1 hereafter. The location of orf O is without precedent in the structure of retroviruses. Orf F is unique in that it is half encoded by the U3 element of the LTR. Both orfs have "strong" initiator codons (Kozak 1984) near their 5' ends and can encode proteins of 192 aminoacids (MWcalc=22487) and 206 aminoacids (MWcalc=23316) respectively. Both putative proteins are hydrophilic (pO 49% polar, 15.1% Arg+Lys: PF 46% polar, 11% Arg+Lys) and are therefore unlikely to be associated directly with membrane. The function for the putative proteins pO and pF cannot be predicted as no homology was found by screening protein sequence data banks. Between orf F and the pX protein of HTLV-1 there is no detectable homology. Furthermore their hydrophobicity/hydrophilicity profiles are completely different. It is known that retroviruses can transduce cellular genes notably proto-oncogenes (Weinberg 1982)). We suggest that orfs O and F represent exogenous genetic material and not some vestige of cellular DNA because (I) LAV DNA does not hybridize to the human genome under stringent conditions (Alizon et al., 1984). (II) their codon usage is comparable to that of the gag, pol and env genes (data not shown).

The organization of a reconstructed LTR and viral flanking elements are shown schematically in FIG. 6. The LTR is 638 bp long and displays usual features (Chen and Barker 1984): (I) It is bounded by an inverted repeat (5'ACTG) including the conserved TG dinucleotide (Temin 1981). (II) Adjacent to 5'LTR is the tRNA primer binding site (PBS), complementary to tRNA$_3^{lys}$ (Raba et al., 1979), (III) adjacent to 3'LTR is a perfect 15 bp polypurine tract. The other three polypurine tracts observed between nucleotides 8200–8800 are not followed by a sequence which is complementary to that just preceding the PBS. The limits of U5, R and U3 elements were determined as follows. U5 is located between PBS and the polyadenylation site established from the sequence of the 3' end of oligo(dT)-primed LAVcDNA (Alizon et al., 1984). Thus U5 is 84 bps long. The length of R+U5 was determined by synthesizing tRNA-primed LAV cDNA. After alkaline hydrolysis of the primer, R+U5 was found to be 181±1 bp. Thus R is 97 bps long and the capping site at its 5' end can be located. Finally U3 is 456 bp long. The LAV LTR also contains characteristic regulatory elements: a polyadenylation signal sequence AATAAA 19 bp from the R-U5 junction and the sequence ATATAAG which is very likely the TATA box, 22 bps 5' of the cap site. There are no longer direct repeats within the LTR. Interestingly the LAV LTR shows some similarities to that of the mouse mammary tumour virus (MMTV) Donehower et al., 1981). They both use tRNA$_3^{lys}$ as a primer for (−) strand synthesis whereas all other exogenous mammalian retroviruses known to date use tRNA$^{Pro}$ (Chen and Barker 1984). They possess very similar polypurine tracts (that of LAV is AAAA-GAAAAGGGGG while that of MMTV is AAAAAAGAAAAAGGGGG). It is probable that the viral (+) strand synthesis is discontinuous since the polypurine tract flanking the U3 element of the 3' LTR is found exactly duplicated in the 3end of orf pol, at 4331–4336. In addition, MMTV and LAV are exceptional in that the U3 element can encode an orf. In the case of MMTV, U3 contains the whole orf while in LAV, U3 contains 110 codons of the 3' half of orf F.

The LAV long terminal repeat (LTR) is diagrammatically represented in FIG. 6. As mentioned the LTR was reconstructed from the sequence of λJ19 by juxtaposing the sequences adjacent to the HindIII cloning sites.

Sequencing of oligo(dT) primed LAV DNA clone pLAV75 (Alizon et al., 1984) rules out the possibility of clustered HindIII sites in the R region of LAV. LTR are limited by an inverted repeat sequence (IR). Both of the viral elements flanking the LTR have been represented=tRNA primer binding site (PBS) for 5' LTR and polypurine track (PU) for 3' LTR. Also indicated are a putative TATA box, the cap site, polyadenylation signal (AATAAA) and polyadenylation site (CAA). The location of the open reading frame F (648 nucleotides) is shown above the LTR schema.

The LTR (long terminal repeats) can also be defined as lying between position 8560 and position 160 (end extending over position 9097/1). As a matter of fact the end of the genome is at 9097 and, because of the LTR structure of the retrovirus, links up with the beginning of the sequence Hind III
CTCAATAAAGCTTGCCTTG

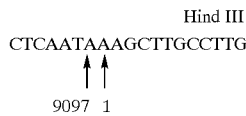

9097  1

Table 1 sums up the locations and sizes of viral open reading frames. The nucleotide coordinates refer to the first base of the first triplet (1$^{st}$ triplet) of the first methionine initiation codon (Met) and of the stop codon (stop). The number of aminoacids and calculated molecular weights are those calculated for unmodified precursor products starting at the first methionine through to the end with the exception of pol where the size and MW refer to that of the whole orf.

TABLE 1

Location and sizes of viral open reading frames.

| orf | 1$^{st}$ triplet | Met | stop | No amino acids | MW calc |
|---|---|---|---|---|---|
| gag | 312 | 336 | 1836 | 500 | 55841 |
| pol | 1631 | 1934 | 4640 | (1003) | (113629) |
| orf Q | 4554 | 4587 | 5163 | 192 | 22487 |
| env | 5746 | 5767 | 8350 | 861 | 97376 |
| orf F | 8324 | 8354 | 8972 | 206 | 23316 |

The invention concerns more particularly all the DNA fragments which have been more specifically referred to hereabove and which correspond to open reading frames. It will be understood that the man skilled in the art will be able to obtain them all, for instance by cleaving an entire DNA corresponding to the complete genome of a LAV species, such as by cleavage by a partial or complete digestion thereof with a suitable restriction enzyme and by the subsequent recovery of the relevant fragments. The different DNAs disclosed above can be resorted to also as a source of suitable fragments. The techniques disclosed hereafter for the isolation of the fragments which were then included in the plasmids referred to hereabove and which were then used for the DNA sequencing can be used.

Of course other methods can be used. Some of them have been exemplified in British Application Nr. 8423659 filed on Sep. 19, 1984. Reference is for instance made to the following methods.

a) DNA can be transfected into mammalian cells with appropriate selection markers by a variety of techniques, calcium phosphate precipitation, polyethylene glycol, protoplast-fusion, etc.

b) DNA fragments corresponding to genes can be cloned into expression vectors for E. coli, yeast- or mammalian cells and the resultant proteins purified.

c) The proviral DNA can be "shot-gunned" (fragmented) into procaryotic expression vectors to generate fusion polypeptides. Recombinant producing antigenically competent fusion proteins can be identified by simply screening the recombinants with antibodies against LAV antigens.

The invention further refers more specifically to DNA recombinants, particularly modified vectors, including any of the preceding DNA sequences and adapted to transform corresponding microorganisms or cells, particularly eucaryotic cells such as yeasts, for instance saccharomyces cerevisiae, or higher eucaryotic cells, particularly cells of mammals, and to permit expression of said DNA sequences in the corresponding microorganisms or cells. General methods of that type have been recalled in the abovesaid British Patent application Nr. 8429099 filed on Nov. 16, 1984.

More particularly the invention relates to such modified DNA recombinant vectors modified by the abovesaid DNA sequences and which are capable of transforming higher eucaryotic cells particularly mammalian cells. Preferably any of the abovesaid sequences are placed under the direct control of a promoter contained in said vectors and which is recognized by the polymerases of said cells, such that the first nucleotide codons expressed correspond to the first triplets of the above-defined DNA-sequences. Accordingly this invention also relates to the corresponding DNA fragments which can be obtained from LAV genomes or corresponding cDNAs by any appropriate method. For instance such a method comprises cleaving said LAV genomes or cDNAs by restriction enzymes preferably at the level of restriction sites surrounding said fragments and close to the opposite extremities respectively thereof, recovering and identifying the fragments sought according to sizes, if need be checking their restriction maps or nucleotide sequences (or by reaction with monoclonal antibodies specifically directed against epitopes carried by the polypeptides encoded by said DNA fragments), and further if need be, trimming the extremities of the fragment, for instance by an exonucleolytic enzyme such as Bal31, for the purpose of controlling the desired nucleotide-sequences of the extremities of said DNA fragments or, conversely, repairing said extremities with Klenow enzyme and possibly ligating the latter to synthetic polynucleotide fragments designed to permit the reconstitution of the nucleotide extremities of said fragments. Those fragments may then be inserted in any of said vectors for causing the expression of the corresponding polypeptide by the cell transformed therewith. The corresponding polypeptide can then be recovered from the transformed cells, if need be after lysis thereof, and purified, by methods such as electrophoresis. Needless to say that all conventional methods for performing these operations can be resorted to.

The invention also relates more specifically to cloned probes which can be made starting from any DNA fragment according to this invention, thus to recombinant DNAs containing such fragments, particularly any plasmids amplifiable in procaryotic or eucaryotic cells and carrying said fragments.

Using the cloned DNA fragments as a molecular hybridization probe—either by labeling with radionucleotides or with fluorescent reagents—LAV virion RNA may be detected directly in the blood, body fluids and blood products (e.g., of the antihemophilic factors such as Factor VIII concentrates) and vaccines, i.e. hepatitis B vaccine. It has already been shown that whole virus can be detected in culture supernatants of LAV producing cells. A suitable method for achieving that detection comprises immobilizing virus onto a support, e.g. nitrocellulose filters, etc., disrupting the virion and hybridizing with labeled (radiolabeled or "cold" fluorescent- or enzyme-labeled) probes. Such an approach has already been developed for Hepatitis B virus in peripheral blood (according to SCOTTO J. et al. Hepatology (1983), 3, 379–384).

Probes according to the invention can also be used for rapid screening of genomic DNA derived from the tissue of patients with LAV related symptoms, to see if the proviral DNA or RNA is present in host tissue and other tissues.

A method which can be used for such screening comprises the following steps: extraction of DNA from tissue, restriction enzyme cleavage of said DNA, electrophoresis of the fragments and southern blotting of genomic DNA from tissues, subsequent hybridization with labeled cloned LAV provival DNA. Hybridization in situ can also be used.

Lymphatic fluids and tissues and other non-lymphatic tissues of humans, primates and other mammalian species can also be screened to see if other evolutionary related retrovirus exist. The methods referred to hereabove can be used, although hybridization and washings would be done under non stringent conditions.

The DNAs or DNA fragments according to the invention can be used also for achieving the expression of LAV viral antigens for diagnostic purposes.

The invention relates generally to the polypeptides themselves, whether synthesized chemically isolated from viral preparation or expressed by the different DNAs of the inventions, particularly by the ORFs or fragments thereof, in appropriate hosts, particularly procaryotic or eucaryotic hosts, after transformation thereof with a suitable vector previously modified by the corresponding DNAs.

More generally, the invention also relates to any of the polypeptide fragments (or molecules, particularly glycoproteins having the same polypeptidic backbone as the polypeptides mentioned hereabove) bearing an epitope characteristic of a LAV protein or glycoprotein, which polypeptide or molecule then has N-terminal and C-terminal extremities respectively either free or, independently from each other, covalently bond to aminoacids other than those which are normally associated with them in the larger polypeptides or glycoprotein of the LAV virus, which last mentioned aminoacids are then free or belong to another polypeptidic sequence. Particularly the invention relates to hybrid polypeptides containing any of the epitope-bearing-polypeptides which have been defined more specifically hereabove, recombined with other polypeptides fragments normally foreign to the LAV proteins, having sizes sufficient to provide for an increased immunocenicity of the epi-tope-bearing-polypeptide yet, said foreign polypeptide fragments either being immunogenically inert or not interfering with the immunogenic properties of the epitope-bearing-polypeptide.

Such hybrid polypeptides which may contain up to 150, even 250 aminoacids usually consist of the expression products of a vector which contained ab into a nucleic acid sequence expressible under the control of a suitable promoter or replicon in a suitable host, which nucleic acid sequence had however beforehand been modified by insertion therein of a DNA sequence encoding said epitope-bearing-polypeptide.

Said epitope-bearing-polypeptides, particularly those whose N-terminal and C-terminal aminoacids are free, are also accessible by chemical synthesis, according to techniques well known in the chemistry of proteins.

The synthesis of peptides in homogeneous solution and in solid phase is well known.

In this respect, recourse may be had to the method of synthesis in homogeneous solution described by Houben-weyl in the work entitled "Methoden der Organischen Chemie" (Methods of Organic Chemistry) edited by E. WUNSCH., vol. 15-I and II, THIEME, Stuttgart 1974.

This method of synthesis consists of successively condensing either the successive aminoacids in twos, in the appropriate order or successive peptide fragments previously available or formed and containing already several aminoacyl residues in the appropriate order respectively. Except for the carboxyl and amino groups which will be engaged in the formation of the peptide bonds, care must be taken to protect beforehand all other reactive groups borne by these aminoacyl groups or fragments. However, prior to the formation of the peptide bonds, the carboxyl groups are advantageously activated, according to methods well known in the synthesis of peptides. Alternatively, recourse may be had to coupling reactions bringing into play conventional coupling reagents, for instance of the carbodilmide type, such as 1-ethyl-3-(3-dimethyl-aminopropyl)-carbodiimide. When the aminoacid group used carries an additional amine group (e.g., lysine) or another acid function (e.g., glutamic acid), these groups may be protected by carbobenzoxy or t-butyloxycarbonyl groups, as regards the amine groups, or by t-butylester groups, as regards the carboxylic groups. Similar procedures are available for the protection of other reactive groups. For example, SH group (e.g. in cysteine) can be protected by an acetamidomethyl or paramethoxybenzyl group.

In the case of progressive synthesis, aminoacid by aminoacid, the synthesis starts preferably by the condensation of the C-terminal aminoacid with the aminoacid which corresponds to the neighboring aminoacyl group in the desired sequence and so on, step by step, up to the N-terminal aminoacid. Another preferred technique can be relied upon is that described by R. D. Merrifield in "Solid Phase Peptide Synthesis" (J. Am. Chem. Soc., 45, 2149–2154).

In accordance with the Merrifield process, the first C-terminal aminoacid of the chain is fixed to a suitable porous polymeric resin, by means of its carboxylic group, the amino group of said aminoacid then being protected, for example by a t-butyloxycarbonyl group.

When the first C-terminal aminoacid is thus fixed to the resin, the protective group of the amine group is removed by washing the resin with an acid, i.e. trifluoroacetic acid, when the protective group of the amine group is a t-butyloxycarbonyl group.

Then the carboxylic group of the second aminoacid which is to provide the second aminoacyl group of the desired peptidic sequence, is coupled to the deprotected amine group of the C-terminal aminoacid fixed to the resin. Preferably, the carboxyl group of this second aminoacid has been activated, for example by dicyclohexylcarbodimide, while its amine group has been protected, for example by a t-butyloxycarbonyl group. The first part of the desired peptide chain, which comprising the first two aminoacids, is thus obtained. As previously, the amine group is then deprotected, and one can further proceed with the fixing of the next aminoacyl group and so forth until the whole peptide sought is obtained.

The protective groups of the different side groups, if any, of the peptide chain so formed can then be removed. The peptide sought can then be detached from the resin, for example, by means of hydrofluoric acid, and finally recovered in pure form from the acid solution according to conventional procedures.

As regards the peptide sequences of smallest size and bearing an epitope or immunogenic determinant, and more particularly those which are readily accessible by chemical synthesis, it may be required, in order to increase their in vivo immunogenic character, to couple or "conjugate" them covalently to a physiologically acceptable and non toxic carrier molecule.

By way of examples of carrier molecules or macromolecular supports which can be used for making the conjugates according to the invention, will be mentioned natural proteins, such as tetanic toxoid, ovalbumin, serum-albumins, hemocyanins, etc. Synthetic macromolecular carriers, for example polysines or poly(D-L-alanine)-poly (L-lysine)s, can be used too.

Other types of macromolecular carriers which can be used, which generally have molecular weights higher than 20,000, are known from the literature.

The conjugates can be synthesized by known processes, such as described by Frantz and Robertson in "Infect. and Immunity", 33, 193–198 (1981), or by P. E. Kauffman in Applied and Environmental Microbiology, October 1981, Vol. 42, n 4, 611–614.

For instance the following coupling agents can be used: glutaric aldehyde, ethyl chloroformate, water-soluble carbodiumides (N-ethyl-N'(3-dimethylamino-propyl) carbodiimide, HCl, diisocyanates, bis-diazobenzidine, di- and trichloro-s-triazines, cyanogen bromides, benzaquinone, as well as coupling agents mentioned in "Scand. J. Immunol.," 1978, vol. 8, p. 7–23 (Avrameas, Ternynck, Guesdon).

Any coupling process can be used for bonding one or several reactive groups of the peptide, on the one hand and one or several reactive groups of the carrier, on the other hand. Again coupling is advantageously achieved between carboxyl and amine groups carried by the peptide and the carrier or vice-versa in the presence of a coupling agent of the type used in protein synthesis, i.e. 1-ethyl-3-(32-dimethylaminonpropyl)-carbodiimide, N-hydroxybenzotriazole, etc. Coupling between amine groups respectively borne by the peptide and the carrier can also be made with glutaraldehyde, for instance, according to the method described by BOQUET, P. et al. (1982) Molec. Immunol., 19, 1441–1549, when the carrier is hemocyanin.

The immunogenicity of epitope-bearing-peptides can also be reinforced, by oligomerisation thereof, for example in the presence of glutaraldehyde or any other suitable coupling agent. In particular, the invention relates to the water soluble immunogenic oligomers thus obtained, comprising particularly from 2 to 10 monomer units.

The glycoproteins, proteins and polypeptides (generally designated hereafter as "antigens" of this invention, whether obtained in a purified state from LAV virus preparations or—as concerns more particularly the peptides—by chemical synthesis, are useful in processes for the detection of the presence of anti-LAV antibodies in biological media, particularly biological fluids such as sera from man or animal, particularly with a view of possibly diagnosing LAS or AIDS.

Particularly the invention relates to an in vitro process of diagnosis making use of an envelope glycoprotein (or of a polypeptide bearing an epitope of this glycoprotein) for the detection of anti-LAV antibodies in the serums of persons who carry them. Other polypeptides—particular those carrying an epitope of a core protein - can be used too.

A preferred embodiment of the process of the invention comprises:

depositing a predetermined amount of one or several of said antigens in the cups of a titration microplate;

introducing of increasing dilutions of the biological fluid, i.e. serum to be diagnosed into these cups;

incubating the microplate;

washing carefully the microplate with an appropriate buffer;

adding into the cups specific labeled antibodies directed against blood immunoglobulin and detecting the antigen-antibody-complex formed, which is then indicative of the presence of LAV antibodies in the biological fluid.

Advantageously the labelling of the anti-immunoglobulin antibodies is achieved by an enzyme selected from among those which are capable of hydrolyzing a substrate, which substrate undergoes a modification of its radiation-absorption, at least within a predetermined band of wavelengths. The detection of the substrate, preferably comparatively with respect to a control, then provides a measurement of the potential risks or of the effective presence of the disease.

Thus preferred methods immuno-enzymatic or also immunofluorescent detections in particular according to the ELISA technique. Titrations may be determinations by immunofluorescence or direct or indirect immunoenzymatic determinations. Quantitative titrations of antibodies on the serums studied can be made.

The invention also relates to the diagnostic kits themselves for the in vitro detection of antibodies against the LAV virus, which kits comprise any of the polypeptides identified herein, and all the biological and chemical reagents, as well as equipment, necessary for performing diagnostic assays. Preferred kits comprise all reagents required for carrying out ELISA assays. Thus preferred kits will include, in addition to any of said polypeptides, suitable buffers and anti-human immunoglobulins, which anti-human immunoglobulins are labeled either by an immunofluorescent molecule or by an enzyme. In the last instance preferred kits then also comprise a substrate hydrolysable by the enzyme and providing a signal, particularly modified absorption of a radiation, at least in a determined wavelength, which signal is then indicative of the presence of antibody in the biological fluid to be assayed with said kit.

The invention also relates to vaccine compositions whose active principle is to be constituted by any of the antigens, i.e. the hereabove disclosed polypeptides whole antigens, particularly the purified gp110 or immunogenic fragments thereof, fusion polypeptides or oligopeptides in association with a suitable pharmaceutical or physiologically acceptable carrier.

A first type of preferred active principle is the gp110 immunogen.

Other preferred active principles to be considered in that fields consist of the peptides containing less than 250 aminoacid units, preferably less than 150, as deducible for the complete genomes of LAV, and even more preferably those peptides which contain one or more groups selected from Asn-X-Ser and Asn-X-Ser as defined above. Preferred peptides for use in the production of vaccinating principles are peptides (a) to (f) as defined above. By way of example having no limitative character, there may be mentioned that suitable dosages of the vaccine compositions are those which are effective to elicit antibodies in vivo, in the host, particularly a human host. Suitable doses range from 10 to 500 micrograms of polypeptide, protein or glycoprotein per kg, for instance 50 to 100 micrograms per kg.

The different peptides according to this invention can also be used themselves for the production of antibodies, preferably monoclonal antibodies specific of the different peptides respectively. For the production of hybridomas secreting said monoclonal antibodies, conventional production and screening methods are used. These monoclonal antibodies, which themselves are part of the invention then provide very useful tools for the identification and even determination of relative proportions of the different polypeptides or proteins in biological samples, particularly human samples containing LAV or related viruses.

The invention further relates to the hosts (procaryotic or eucaryotic cells) which are transformed by the above mentioned recombinants and which are capable of expressing said DNA fragments.

Finally the invention also concerns vectors for the transformation of eucaryotic cells of human origin, particularly lymphocytes, the polymerases of which are capable of recognizing the LTRs of LAV. Particularly said vectors are characterized by the presence of a LAV LTR therein, said LTR being then active as a promoter enabling the efficient transcription and translation in a suitable host of a DNA insert coding for a determined protein placed under its controls.

Needless to say that the invention extends to all variants of genomes and corresponding DNA fragments (ORFs) having substantially equivalent properties, all of said genomes belonging to retroviruses which can be considered as equivalents of LAV. It must be understood that the claims which follow are also intended to cover all equivalents of the products (glycoproteins, polypeptides, DNAs, etc.), whereby an equivalent is a product, i.e. a polypeptide which may distinguish from a determined one defined in any of said claims, say through one or several aminoacids, while still having substantially the same immunological or immunogenic properties. A similar rule of equivalency shall apply to the DNAs, it being understood that the rule of equivalency will then be tied to the rule of equivalency pertaining to the polypeptides which they encode.

It will also be understood that all the literature referred to hereinbefore or hereinafter, and all patent applications or patents not specifically identified herein but which form counterparts of those specifically designated herein must be considered as incorporated herein by reference.

REFERENCES

Alizon, M., Sonigo, P., Barré-Sinoussi, F., Chermann, J. C., Tiollais, P., Montagnier, L., and Wain-Hobson, S. (1 984). Molecular cloning of lymphadenopathy-associated virus. Nature, in press.

Arya, S. K., Gallo, R. C., Hahn, B. H., Shaw, G. M., Popovic, M., Salahuddin, S. Z., and Wong-Staal, F. (1984). Homology of genome of AIDS-associated virus with genomes of human T-cell leukemia lymphoma viruses. Science 225, 927–930.

Barré-Sinoussi, F., Cherrnann, J. C., Rey, F., Nugeybe, M. T., Chamaret, S., Gruest, J., Dauguet, C., Axler-Blin, C., Vézinet-Brun, F., Rouzioux, C., Rozenbaum, W., and Montagnier, L. (1983). Isolation of a T-lymphotropic retrovirus from a patient at risk of Acquired Immune Deficiency Syndrome (AIDS). Science 220, 868–870.

Biggen, M. D., Gibson, T. J., and Hong, G. F. (1983). Buffer gradient gels and $^{35}$S label as an aid to rapid DNA sequence determination. Proc. Natl. Acad. Sci. USA 80, 3963–3965.

Bird, A. P. (1980). DNA methylation and the frequency of CpG in animal DNA. Nucl. Acids Res. 8, 1499–1504.

Brun-Vézinet, F., Rouzioux, C., Barré-Sinoussi, F., Klatzmann, D., Saimot, A. G., Rozembaum, W., Montagnier, L., and Chermann, J. C. (1984). Detection of IgG antibodies to lymphadenopathy associated virus (LAV) by ELISA, in patients with acquired immunodeficiency syndrome of lymphadenopathy syndrome. Lancet I, 1253–1256.

Chen, H. R. and Barker, W. C. (1984). Nucleotide sequences of the retroviral long terminal repeats and their adjacent regions. Nucl. Acids Res. 12, 1767–1778.

Chen, I. S. Y., Mc Laughlin, J., Gasson, J. C., Clark, S. C., and Golde, D. W. (1983). Molecular characterization of genome of a novel human T-cell leukaemia virus. Nature 305, 502–505.

Chiu, I. M., Callahan, R., Tronick, S. R., Scholm, J., and Aaronson, S. A. (1984). Major pol gene progenitors in the evolution of oncornaviruses. Science 223, 364–370.

Cianciolo, G. J., Kipnis, R. J., and Snyderman, R. (1984). Similarity between plSE of murine and feline viruses and p21 of HTLV. Nature 311, 515.

Daly, H. M. and Scott, G. L. (1983). Fatal AIDS in a haemophiliae in the U. K. Lancet II, 1190.

Dittmar, K. J. and Moelling, K. (1978). Biochemical properties of P15-associated protease in an avion RNA tumor virus. J. Virol. 28, 106–118.

Donehower, L. A., Huang, A. L., and Hager, G. L. (1981). Regulatory and coding potential of the mouse mammary tumour virus long terminal redundancy. J. Virol. 37, 226–238.

Gottlieb, M. S., Schroff, R., Schanler, H. M., Weisman, J. D., Fan, P. T., Wolf, R. A., Saxon, A. (1981). Pneumocytis carinii pneumonia and mucosal candidiasis in previously healthy homosexual men: Evidence of a new acquired cellular immuno-deficiency. N. Engl. J. Med. 305, 1426–1431.

Hahn, B. H., Shaw, G. M., Arya, S. U., Popovic, M., Gallo, R. C., and Wong-Stall, F. (1984). Molecular cloning and characterization of the HTLV-III virus associated with AIDS. Nature 312, 166–169.

Harris, J. D., Scott, J. V., Taylor, B., Brahic, M., Stowring, L., Ventura, P., Haase, A. T., and Peluso, R. (1981). Visna virus DNA: discovery of a novel gapped structure. Virology 113, 573–583.

Kiyokawa, T., Yoshikura, H., Hattori, S., Secki, M., and Yoshida, M. (1984) Envelope proteins of human T-cell leukemia virus : expression in Escherischia coli and its application to studies of env gene functions. Proc. Natl. Acad. Sci. USA 81, 6202–6206.

Katzmann, D., Barré-Sinoussi, F., Nugeyre, M. T., Dauguet, C., Vilmer, E., Griscelli, C., Brun-Vézinet, F., Rouzioux, C., Gluckman, J. C., Chermann, J. C., and Montagnier, L. (1984). Selective tropism of lymphadenopathy associated virus (LAV) for helper-inducer T-lymphocytes. Sciences 225, 59–63.

Kozak, M. (1984). Compilation and analysis of sequences upstream from the transcriptional start site in eucaryotic mRNAs. Nucl. Acids Res. 12, 857–872.

Levy, J. A., Hoffman, A. D., Kramer, S. M., Lanois, J. A., Shimabukuro, J. M., and Oskiro, L. S. (1984). Isolation of lymphocytopathic retroviruses from San Francisco patients with AIDS. Science 225, 840–842.

Masur, H., Michelis, M. A., Greene, J. B., Onavato, I., Van de Stowe, R. A., Holzman, R. S., Wormser, G., Brettman, L., Lange, M., Murray, H. W., Cunningham-Rundles, S. (1981). An outbreak of community-acquired pneumocystis carinii pneumonia: Initial manifestation of cellular immune dysfunction. N. Engl. J. Med. 305, 1431–1438.

Misra, T. K., Grandgenett, D. P., and Parsons, J. T. (1982). Avian retrovirus pp32 DNA-binding protein. I. Recognition of specific sequences on retrovirus DNA terminal repeats. J. Virol. 44, 330–343.

Montagnier, L., et al. (1984). A new human T-lymphotropic retrovirus: characterization and possible role in lymphadenopathy and acquired immune deficiency syndromes. In human T-cell leukemia/lymphoma viruses. R. C. Gallo, M. Essex, and L. Gross, eds. (Cold Spring Laboratory, New York), pp. 363–370.

Oroszlan, S., Copeland, T. D., Kalyanaraman, V. S., Sarngadharan, M. G., Schultz, A. M., and Gallo, R. C. (1984). Chemical analysis of human T-cell leukemia virus structural proteins. In HTLVS (R. C. Gallo, M. E. Essex, and L. Gross, eds.) Cold Spring Laboratory, New York, pp. 101–110.

Piot, P., Quinn, T. C., Taelmann, H., Feinsod, F. M., et al. (1984). Acquired immunodeficiency syndrome in a heterosexual population in Zaire. Lancet II, 65–69.

Popovic, M., Sarngadharan, M. G., Read, E., and Gallo, R. C. (1984). Detection, isolation, and continuous production of cytopathic retroviruses (HTLV-III) from patients with AIDS and pre-AIDS. Science 224, 497–500.

Querat, G., Barhan, N., Sauze, N., Filippi P., Vigne, R., Russo, P., and Vitu, C. (1984). Highly lytic and persistent lentiviruses naturally present in sheep with progressive pneumonia are genetically distinct. J. Virol. 52, 672–679.

Raba, M., Limburg, K., Burghagen, M., Katze, J. R., Simsek, M., Heckman, J. E., Rajbhandary, U. L., and Gross, H. J. (1979). Nucleotide sequence of three isoaccepting lysine tRNAs from rabbit liver and SV40-transformed mouse fibroblasts. Eur. J. Biochem. 97, 305–318.

Rice, N. R., Stephens, R. M., Couez, D., Deschamps, J., Kettmann, R., Bumy, A., and Gilden, R. V. (1984). The nucleotide sequence of the env gene and post-env region of bovine leukemia virus. Virology 138, 82–93.

Sagata, N., Yasunaga, T., Ogawa, Y., Tsuzuku-Kawamura, J., and Ikawa, Y. (1984). Bovine leukemia virus: Unique structural features of its long terminal repeats and its evolutionary relationship to human T-cell leukemia virus. Proc. Natl. Acad. Sci. USA 81, 4741–4745.

Sanger, F., Nicklen, S., and Coulsen, A. R. (1 977). DNA sequencing with chain terminating inhibitors. Proc. Natl. Acad. Sci. USA 74, 5463–5467.

Schwartz, D. E., Tizard, R., and Gilbert, W. (1983). Nucleotide sequence of Rous sarcoma virus. Cell 32, 853–869.

Schuipbach, J., Popovic, M., Gilden, R. V., Gonda, M. A., Sarngadharan, M. G., and Gallo, R. C. (1984). Serological analysis of a subgroup of human T-lymphotropic retroviruses (HTLV-III) associated with AIDS. Science 224, 503–505.

Seiki, M., Hattori, S., Hirayama, Y., and Yoshida, M. (1983). Human adult T-cell leukemia virus complete nucleotide sequence of the provirus genome integrated in leukemia cell DNA. Proc. Natl. Acad. Sci. 80, 3618–3622.

Shaw, G. M., Hahn, B. H., Arya, S. K., Groopman, J. E., Gallo, R. C., and Wong-Staal, F. (1984). Molecular characterization of human T-cell leukemia (lymphotropic) virus type III in the Acquired Immune Deficiency Syndrome. Science 226, 1165–1171.

Shimotohno, K., and Temin, H. M. (1982). Spontaneous variation and synthesis in the U3 region of the long terminal repeat of avion retroviruses. J. Virol. 41, 163–171.

Shimotohno, K., Golde, D. M., Miwa, M., Sugimura, T., and Chen, I. S. Y. (1984). Nucleotide sequence analysis of the long terminal repeat of human T-cell leukemia virus type II. Proc. Natl. Acad. Sci. USA 81, 1079–1083.

Shinnick, T. M., Lerner, R. A., and Sutcliffe, J. G. (1981). Nucleotide sequence of Moloney murine leukemia viruses. Nature 293, 543–548.

Srinivasan, A., Reddy, E. P., Dunn, C. Y., and Aaronson, S. A. (1984). Molecular dissection of transcriptional control elements with the long terminal repeat of retrovirus. Science 223, 286–289.

Staden, R. (1982). Automation of the computer handling of gel reading data produced by the shotgun method of DNA sequencing. Nucl. Acids. Res. 10, 4731–4751.

Temin, H. (1981). Structure, variation and synthesis of retroviris long terminal repeat. Cell 27, 1–3.

Weinberg, R. A. (1982). Fewer and fewer oncogenes. Cell 30, 3–9.

What is claimed is:

1. A chemically synthesized env peptide of Human Immunodeficiency Virus (HIV) of less than 150 amino acid residues, wherein the peptide comprises the sequence:

Val Gln Ala Arg Gln Leu Leu Ser Gly Ile Val Gln Gln Gln Asn Asn Leu Leu Arg Ala Ile Glu Ala Gln Gln His Leu.

2. A chemically synthesized env peptide of Human Immunodeficiency Virus (HIV) of less than 150 amino acid residues, wherein the peptide comprises the sequence:

Ala Val Glu Arg Tyr Leu Lys Asp Gln Gln.

3. A chemically synthesized env peptide of Human Immunodeficiency Virus (HIV) of less than 150 amino acid residues, wherein the peptide comprises the sequence:

Pro Trp Asn Ala Ser Trp Ser Asn Lys Ser.

4. A chemically synthesized env peptide of Human Immunodeficiency Virus (HIV) of less than 150 amino acid residues, wherein the peptide comprises the sequence:

Leu Ile Glu Glu Ser Gln Asn Gln Gln Glu Lys Asn Glu Gln Glu Leu Leu Glu Leu Asp Lys Trp Ala.

5. A chemically synthesized env peptide of Human Immunodeficiency Virus (HIV) of less than 150 amino acid residues, wherein the peptide comprises the sequence:

Arg Val Arg Gln Gly Tyr Ser Pro Leu Ser Phe Gln Thr His Leu Pro Thr Pro Arg Gly Pro Asp Arg Pro Glu Gly Ile Glu Glu Glu Gly Gly Glu Arg Asp Arg Asp Arg Ser Ile.

6. An in vitro diagnostic method for the detection of the presence or absence of antibodies that bind to antigens of HIV-1 retrovirus comprising:

(a) contacting at least one peptide of any one of claims 1 to 5 with a biological fluid for a time and under conditions sufficient for said peptide and antibody in the biological fluid to form a peptide-antibody complex;

(b) detecting the formation of the peptide-antibody complex by comparing said formation of the peptide-antibody complex with a control sample, wherein the formation of the peptide-antibody complex is correlated with the presence of antibodies that bind to antigens of HIV-1 retrovirus in said biological sample.

* * * * *

UNITED STATES PATENT AND TRADEMARK OFFICE
CERTIFICATE OF CORRECTION

PATENT NO. : 6,440,657 B1
DATED : August 27, 2002
INVENTOR(S) : Luc Montagnier, Bernard Krust, Solange Chamaret, Francois Clavel,
Jean-Claude Chermann, Francoise Barresinoussi, Marc Alizon, Pierre Sonigo,
Stewart Cole, Olivier Danos and Simon Wain-Hobson It is certified that error appears in the above-identified patent and that said Letters Patent is hereby corrected as shown below:

<u>Title page,</u>
Item [12], "Montangnier et al." should read -- Montagnier et al. --.

Item [75], Inventors, "Luc Montangnier" should read -- Luc Montagnier --.

Signed and Sealed this

Fifteenth Day of October, 2002

*Attest:*

*Attesting Officer*

JAMES E. ROGAN
*Director of the United States Patent and Trademark Office*